(12) United States Patent
Lövgren

(10) Patent No.: US 7,989,193 B2
(45) Date of Patent: Aug. 2, 2011

(54) COMPOSITIONS AND METHODS FOR PRODUCING GAMMA-CARBOXYLATED PROTEINS

(75) Inventor: Ann Lövgren, Mölndal (SE)

(73) Assignee: MedImmune Limited, Cambridge (GB)

( * ) Notice: Subject to any disclaimer, the term of this patent is extended or adjusted under 35 U.S.C. 154(b) by 535 days.

(21) Appl. No.: 11/572,870

(22) PCT Filed: Apr. 10, 2006

(86) PCT No.: PCT/SE2006/000426
§ 371 (c)(1),
(2), (4) Date: Jan. 29, 2007

(87) PCT Pub. No.: WO2006/110083
PCT Pub. Date: Oct. 19, 2006

(65) Prior Publication Data
US 2008/0312127 A1    Dec. 18, 2008

(30) Foreign Application Priority Data

Apr. 13, 2005    (SE) ..................... 0500831

(51) Int. Cl.
C12N 1/20      (2006.01)
C12N 15/00     (2006.01)
C12N 9/00      (2006.01)
C12N 9/02      (2006.01)
C12N 9/14      (2006.01)
C12Q 1/00      (2006.01)
C12Q 1/68      (2006.01)
C12P 21/04     (2006.01)
C07H 21/04     (2006.01)
C07K 1/00      (2006.01)

(52) U.S. Cl. .......... 435/252.3; 435/4; 435/6; 435/69.1; 435/71.1; 435/320.1; 435/189; 435/183; 435/195; 536/23.2; 530/350

(58) Field of Classification Search .................. None
See application file for complete search history.

(56) References Cited

U.S. PATENT DOCUMENTS

| | | | |
|---|---|---|---|
| 4,404,187 A | 9/1983 | Schwinn et al. | |
| 4,599,308 A | 7/1986 | Hamer et al. | |
| 4,784,950 A | 11/1988 | Hagen et al. | |
| 5,118,614 A | 6/1992 | Rybak et al. | |
| 5,122,458 A | 6/1992 | Post et al. | |
| 5,648,254 A | 7/1997 | Mulvihill et al. | |
| 5,866,122 A | 2/1999 | Turecek et al. | |
| 5,958,893 A | 9/1999 | Welsh et al. | |
| 5,965,789 A * | 10/1999 | Lubon et al. ........... 800/14 |
| 6,039,945 A | 3/2000 | Turecek et al. | |
| 6,165,974 A | 12/2000 | Turecek et al. | |
| 6,224,862 B1 | 5/2001 | Turecek et al. | |
| 6,224,864 B1 | 5/2001 | Argoudelis et al. | |
| 6,342,372 B1 * | 1/2002 | Dubensky et al. ........ 435/69.1 |
| 6,413,737 B1 | 7/2002 | Osen et al. | |
| 7,482,141 B2 * | 1/2009 | Stafford et al. ........... 435/69.6 |
| 7,842,477 B2 | 11/2010 | Fenge et al. | |
| 2002/0106381 A1 | 8/2002 | High | |
| 2004/0197858 A1 | 10/2004 | Yonemura et al. | |
| 2005/0164367 A1 | 7/2005 | Fenge et al. | |
| 2008/0045453 A1 | 2/2008 | Drohan et al. | |
| 2008/0312127 A1 | 12/2008 | Lovgren | |
| 2009/0047273 A1 | 2/2009 | Harrysson et al. | |

FOREIGN PATENT DOCUMENTS

| | | |
|---|---|---|
| EP | 0052827 | 6/1982 |
| EP | 0607392 | 7/1994 |
| EP | 0700682 | 3/1996 |
| EP | 1 407 780 A1 | 4/2004 |
| EP | 1405910 | 4/2004 |
| EP | 1405912 | 4/2004 |
| EP | 1676911 | 7/2006 |
| WO | WO 88/03926 A1 | 6/1988 |
| WO | WO 89/12685 A1 | 12/1989 |
| WO | WO 92/01795 | 2/1992 |
| WO | WO 92/19636 A1 | 11/1992 |
| WO | WO 96/34966 A2 | 11/1996 |
| WO | WO 96/34966 A3 | 11/1996 |
| WO | WO 99/033983 | 7/1999 |
| WO | WO 01/04146 | 1/2001 |
| WO | WO 01/07068 | 2/2001 |
| WO | WO 02/29045 A2 | 4/2002 |
| WO | WO 02/29045 A3 | 4/2002 |
| WO | WO 02/29083 A2 | 4/2002 |
| WO | WO 02/29083 A3 | 4/2002 |
| WO | WO 2005/030039 | 4/2005 |
| WO | WO 2005/038019 | 4/2005 |

(Continued)

OTHER PUBLICATIONS

Gamma Glutamyl Carboxylase. UniPro Database. [online], [retrieved on Jan. 14, 2010] Retrieved from the UniPro Database using Internet <URL: http://www.uniprot.org/uniprot/?query=gamma+glutamyl+carboxylase&sort=score>.*
Bandyopadhyay et al., "γ-Glutamyl carboxylation: an extracellular posttranslational modification that antedates the divergence of molluscs, anthropods, and chordates," *PNAS* 99(3):1264-1269 (2002).
Begley et al., "A conserved motif within the vitamin K-dependent carboxylase gene is widely distributed across animal phyla," *J. Biol. Chem.* 275(46):36245-36249 (2000).
Cote et al., "Characterization of a stable form of human meizothrombin derived from recombinant prothrombin (R155A, R271A, and R284A)," *J. Biol. Chem.* 269(15):11374-11380 (1994).
Czerwiec et al., "Expression and characterization of recombinant vitamin K-dependent γ-glutamyl carboxylase from an invertebrate, *Conus textile*," *Eur. J. Biochem.* 269:6162-6172 (2002).

(Continued)

*Primary Examiner* — Yong Pak
(74) *Attorney, Agent, or Firm* — Fish & Richardson P.C.

(57) ABSTRACT

The present invention relates a host cell comprising an expression vector comprising a nucleic acid molecule encoding a protein requiring gamma-carboxylation and associated expression control sequences and a nucleic acid molecule encoding a vitamin K epoxido reductase and associated expression control sequences and a nucleic acid molecule encoding a γ-glutamyl carboxylase and associated control sequences. The invention further relates to a method of producing a protein requiring gamma-carboxylation in high yields.

49 Claims, 3 Drawing Sheets

FOREIGN PATENT DOCUMENTS

| WO | WO 2005/040367 | 5/2005 |
|---|---|---|
| WO | WO 2006/067116 | 6/2006 |
| WO | WO 2006/110083 | 10/2006 |
| WO | WO 2007/065173 | 6/2007 |

OTHER PUBLICATIONS

Fischer et al., "Purification of recombinant human coagulation factors II and IX and protein S expressed in recombinant Vaccinia virus-infected Vero cells," *Journal of Biotechnology* 38:129-136 (1995).

Hallgren et al., "Carboxylase overexpression effects full carboxylation but poor release and secretion of a factor IX: implications for the release of vitamin K-dependent proteins," *Biochemistry* 41:15045-15055 (2002).

Harvey et al., "Mutagenesis of the γ-carboxyglutamic acid domain of human factor VII to generate maximum enhancement of the membrane contact site," *J. Biol. Chem.* 278(10):8363-8369 (2003).

Herlitschka et al., "Overexpression of human prothrombin in permanent cell lines using a dominant selection/amplification fusion marker," *Protein Expression and Purification* 8:358-364 (1996).

Himmelspach et al., "A Fully Recombinant Partial Prothrombin Complex Effectively Bypasses fVII in Vitro and in Vivo," *Thromb Haemost* 88:1003-1011 (2002).

Jorgensen et al., "Expression of completely γ-carboxylated recombinant human prothrombin," *J. Biol. Chem.* 262(14):6729-6734 (1987).

Li et al., "Identification of the gene for vitamin K epoxide reductase", *Nature* 427:541-544 (2004).

Malhotra et al., "The kinetics of activation of normal and γ-carboxyglutamic acid-deficient prothrombins," *J. Biol. Chem.* 260:279-287 (1985).

Rehemtulla et al., "In vitro and in vivo functional characterization of bovine vitamin K-dependent γ-carboxylase expressed in Chinese hamster ovary cells," *Proc. Natl. Acad. Sci.* 90:4611-4615 (1993).

Roddie at al., "Haemostasis and thrombosis: Recombinant coagulation factors," *Blood Reviews* 11:169-177 (1997).

Russo et al., "Biologically active recombinant prothrombin and antithrombin III expressed in a human hepatoma/vaccinia virus system," *Biotechnology and Applied Biochemistry* 14:222-223 (1991).

Russo et al., "Stable expression and purification of a secreted human recombinant prethrombin-2 and its activation to thrombin," *Protein Expression and Purification* 10:214-225 (1997).

Scharrer et al., "Products used to treat hemophilia: evolution of treatment for hemophilia A and B," in: Lee et al., eds., *Textbook of Hemophilia* (New York, Blackwell, 2005), Ch. 23, pp. v-x and 131-135.

Stanley et al., "The propeptides of the vitamin K-dependent proteins possess different affinities for the vitamin K-dependent carboxylase," *J. Biol. Chem.* 274(24):16940-16944 (1999).

Sun et al., "Vitamin K epoxide reductase significantly improves carboxylation in a cell line overexpressing factor X," *Blood* 106(12):3811-3815 (2005).

Vo et al., "Undercarboxylation of recombinant prothrombin revealed by analysis of γ-carboxyglutamic acid using capillary electrophoresis and laser-induced fluorescence," *Febs Letters* 445:256-260 (1999).

Wajih et al., "Engineering of a Recombinant Vitamin K-dependent γ-Carboxylation System with Enhanced γ-Carboxyglutamic Acid Forming Capacity," *J. Biol. Chem.* 280:10540-10547 (2005).

Wajih et al., "Increased Production of Functional Recombinant Human Clotting Factor IX by Baby Hamster Kidney Cells Engineered to Overexpress VKORC1, the Vitamin K 2,3-Expoxide-reducing Enzyme of the Vitamin K Cycle," *J. Biol. Chem.* 280:31603-31607 (2005).

Walker at al., "On a potential global role for vitamin K-dependent γ-carboxylation in animal systems," *J. Biol. Chem.* 276(11):7769-7774 (2001).

Wu et al., "Cloning and expression of the cDNA for human γ-glutamyl carboxylase," *Science* 254:1634-1636 (1991).

Wu et al., "N-Glycosylation contributes to the intracellular stability of prothrombin precursors in the endoplasmic reticulum," *Thrombosis Research* 96:91-98 (1999).

Zhang et al., "Relative Promoter Strengths in Four Human Prostate Cancer Cell Lines Evaluated by Particle Bombardment-Mediated Gene Transfer," *The Prostate*, 51:286-292 (2002).

USPTO Restriction Requirement in U.S. Appl. No. 12/167,614, mailed Apr. 6, 2009, 8 pages.

Fish & Richardson P.C., Amendment in Reply to Restriction Requirement dated Apr. 6, 2009, in U.S. Appl. No. 12/167,614, filed Aug. 4, 2009, 9 pages.

USPTO Restriction Requirement in U.S. Appl. No. 10/964,888, mailed Aug. 9, 2006, 10 pages.

Fish & Richardson P.C., Amendment in Reply to Restriction Requirement dated Aug. 9, 2006, in U.S. Appl. No. 10/964,888, filed Feb. 6, 2007, 11 pages.

USPTO Non-Final Office Action in U.S. Appl. No. 10/964,888, mailed Apr. 19, 2007, 17 pages.

Fish & Richardson P.C., Amendment in Reply to Action dated Apr. 19, 2007, in U.S. Appl. No. 10/964,888, filed Oct. 18, 2007, 26 pages.

USPTO Non-Final Office Action in U.S. Appl. No. 10/964,888, mailed Jan. 28, 2008, 29 pages.

Fish & Richardson P.C., Amendment in Reply to Action dated Jan. 28, 2008, in U.S. Appl. No. 10/964,888, filed Apr. 28, 2008, 22 pages.

USPTO Final Office Action in U.S. Appl. No. 10/964,888, mailed Apr. 3, 2009, 6 pages.

Fish & Richardson P.C., Amendment in Reply to Action dated Apr. 3, 2009, in U.S. Appl. No. 10/964,888, filed Jun. 17, 2009, 15 pages.

USPTO Non-Final Office Action in U.S. Appl. No. 10/964,888, mailed Aug. 21, 2009, 5 pages.

Broun et al., "Catalytic Plasticity of Fatty Acid Modification Enzymes Underlying Chemical Diversity of Plant Lipids," Science, 282:1315-1317 (1998).

Gustafsson et al., "Codon bias and heterologous protein expression," Trends in Biotechnol., 22(7):346-353 (2004).

Kaufman et al., "Expression, Purification, and Characterization of Recombinant γ-Carboxylated Factor IX Synthesized in Chinese Hamster Ovary Cells," J. Biol. Chem., 261:9622-9628 (1986).

Koresawa et al., "Synthesis of a new cre recombinase gene based on optimal codon usage for mammalian systems," J. Biochem., 127:367-372 (2000).

Lucas et al., "High-level production of recombinant proteins in CHO cells using a dicistronic DHFR intron expression vector," Nucleic Acids Research., 24:1774-1779 (1996).

McCawley et al., "Matrix metalloproteinases: they're not just for matrix anymore!" Curr. Opinion Cell Biol., 13:534-540 (2001).

Newby A.C., "Matrix matallaproteinases regulate migration, proliferation, and death . . . " Cardiovascular Res. 69:614-624 (2006).

Seffernick et al., "Melamine Deaminase and Atrazine Chlorohydrolase: 98 Percent Identical but Functionally Different," J. Bacteriol., 183:2405-2410 (2001).

Whisstock et al., "Prediction of protein function from protein sequence and structure" Q. Rev. Biophysics., 36:307-340 (2003).

Witkowski et al., "Conversion of β-Ketoacyl Synthase to a Malonyl Decarboxylase by Replacement of the Active-Site Cysteine with Glutamine" Biochemistry, 38:11643-11650 (1999).

USPTO Non-Final Office Action in U.S. Appl. No. 12/167,614, mailed Sep. 29, 2009, 19 pages.

Gamma Glutamyl Carboxylase. UniPro Database. [online], [retrieved on Jan. 14, 2010] Retrieved from the UniPro Database using Internet <URL: http://www.uniprot.org/uniprot/?query=gamma+glutamyl+carboxylase&sort=score>.

Slimko et al., "Codon optimization of Caenorhabditis elegans GluCl ion channel genes for mammalian cells dramatically improves expression levels," J. Neuroscience Methods, 124:75-81 (2003).

PCT Written Opinion for Application No. PCT/SE2008/050836, dated Jan. 21, 2010, 10 pages.

Nucleotide sequence of human prothrombin. Last modified Oct. 21, 2008, 8 pages.

Amino acid sequence for wild type ecarin. Last modified Jan. 19, 2010, 5 pages.

Fish & Richardson P.C., Amendment in Reply to Action of Sep. 29, 2009, in U.S. Appl. No. 12/167,614, filed Feb. 26, 2010, 26 pages.

Fish & Richardson P.C., Amendment in Reply to Action dated Aug. 21, 2009, in U.S. Appl. No. 10/964,888, filed Nov. 10, 2009, 17 pages.

USPTO Non-Final Office Action in U.S. Appl. No. 10/964,888, mailed Jan. 27, 2010, 9 pages.

USPTO Non-Final Office Action in U.S. Appl. No. 12/167,614, mailed May 25, 2010, 47 pages.

Bajaj et al. "Isolation and Characterization of Human Factor VII. Activation of Factor VII by Factor X" J. Biotechnol. 1981 (256) 253-259.

Bajaj et al. "A Simplified Procedure for Purification of Human Prothrombin, Factor IX and Factor X" Prep. Biochem. 1981 (11) 397-412.

Bentley et al. "Differential Efficiency of Expression of Humanized Antibodies in Transient Transfected Mammalian Cells" Hybridoma. 1998 (17) 559-567.

Bishop et al. "Comparison of Recombinant Human Thrombin and Plasma-Derived Human α-Thrombin" Sem Throm Hem. 2006 (32) 86-97.

Camire et al. "Enhanced γ-Carboxylation of Recombinant Factor X Using a Chimeric Construct Containing the Prothrombin Propeptide" Biochemistry. 2000 (39) 14322-14329.

Clark et al. "The Secreted Protein Discovery Initiative (SPDI), a Large-Scale Effort to Identify Novel Human Secreted and Transmembrane Proteins: A Bioinformatics Assessment" Genome Res. 2003 (13) 2265-2270.

Fair et al. "Biosynthesis and Secretion of Factor VII, Protein C, Protein S, and the Protein C Inhibitor From a Human Hepatoma Cell Line" Blood. 1986 (67) 64-70.

Falkner et al. "High Level Expression of Active Human Prothrombin in a Vaccine Virus Expression System" Thrombosis and Haemostasis. 1992 (68) 119-124.

Hellstern et al. Preface Thrombosis Research. 1999 (95) S1.

Hellstern et al. "Prothrombin Complex Concentrates: Indications, Contraindications, and Risks: A Task Force Summary" Thrombosis Research. 1999 (95) S3-S6.

Hellstern "Production and Composition of Prothrombin Complex Concentrates: Correlation between Composition and Therapeutic Efficiency" Thrombosis Research. 1999 (95) S7-S12.

Kini et al. "The intriguing world of prothrombin activators from snake venom" Toxicon. 2005 (45) 1133-1145.

Köhler "Thrombogenicity of Prothrombin Complex Concentrates" Thrombosis Research. 1999 (95) S13-S17.

Kozak "Point Mutations Define a Sequence Flanking the AUG Initiator Codon That Modulates Translation by Eukaryotic Ribosomes" Cell. 1986 (44) 283-292.

Kozak "Downstream Secondary Structure Facilitates Recognition of Intiator Codons by Eukaryotic Ribosomes" Proceedings of the National Academy of Sciences of the United States of America. 1990 (87) 8301-8305.

Kozak "An analysis of 5'-noncoding sequences from 699 vertebrate messenger RNAs" Nucleic Acids Research. 1987 (15) 8125-8148.

Lingenfelter et al. "Isolation of the Human γ-Carboxylase and a γ-Carboxylase-Associated Protein from Factor IX-Expressing Mammalian Cells" Biochemistry. 1996 (35) 8234-8243.

Melcher et al. "Plasmid vectors with a 5'-hybrid intron facilitate high-level glycoprotein expression in CHO-cells" Biochimica et Biophysica Acta. 2002 (1575) 49-53.

Munns et al. "Vitamin K-dependent synthesis and modification of precursor prothrombin in cultured H-35 hepatoma cells" Proc. Natl. Acad. Sci. 1976 (73) 2803-2807.

Nishida et al. "cDNA cloning and deduced amino acid sequence of prothrombin activator (ecarin) from Kenyan *Echis carinatus* venom" Biochem. 1995 (34) 1771-1778.

Pei et al. "Expression, isolation, and characterization of an active site (serine 528-alanine) mutant of recombinant bovine prothrombin" J. Biol. Chem. 1991 (266) 9598-9604.

Pejler et al. "Thrombin Is Inactivated by Mast Cell Secretory Granule Chymase" J. Biol. Chem. 1993 (268) 11817-11822.

Robertson "Genes Encoding Vitamin-K Epoxide Reductase are Present in *Drosophila* and Trypanosomatid Protists" Genetics. 2004 (168) 1077-1080.

Rost et al. "Mutations in *VKORC1* cause warfarin resistance and multiple coagulation factor deficiency type 2" Nature. 2004 (427) 537-541.

Rouet et al. "A Potent Enhancer Made of Clustered Liver-specified Elements in the Transcription Control Sequences of Human αl-Microglobulin/Bikunin Gene" the Journal of Biological Chemistry. 1992 (267) 20765-20773.

Sadler "K is for koagulation" Nature. 2004 (427) 493-494.

Scharrer "The Need for Highly Purified Products to Treat Hemophilia B" Acta Haematol. 1995 (94) 2-7.

Strausberg et al. "Generation and initial analysis of more than 15,000 full-length human and mouse cDNA sequences" PNAS. 2002 (99) 16899-16903.

Tans et al. "Prothrombin Activation by Snake Venom Proteases" J. Toxicol.-Toxin Reviews. 1993 (12) 155-173.

Umaña et al. "Tetracycline-Regulated Overexpression of Glycosyltransferases in Chinese Hamster Ovary Cells" Biotechnology and Bioengineering. 1999 (65) 542-549.

Wajih et al. "The Inhibitory Effect of Calumenin on the Vitamin K-dependent γ-Carboxylation System" J. Biol. Chem. 2004 (279) 25276-25283.

Wallin et al. "Vitamin K-dependent Carboxylation and Vitamin K Metabolism in Liver" J. Clin. Invest. 1985 (76) 1879-1884.

Wallin et al. "Vitamin K 2,3-epoxide reductase and the vitamin K-dependent γ-carboxylation system" Thrombosis Research. 2003 (108) 221-226.

Wang et al. "The Growth Inhibitory Effects of Vitamins K and Their Actions on Gene Expression" Hepatology. 1995 (22) 876-882.

Yonemura et al. "Preparation of recombinant α-thrombin: high-level expression of recombinant human prethrombin-2 and its activation by recombinant ecarin" J. Biochem. 2004 (135) 577-582.

Fish & Richardson P.C., Amendment in Reply to Restriction Requirement dated Apr. 6, 2009 in U.S. Appl. No. 12/167,614, filed Aug. 4, 2009, 9 pages.

Fish & Richardson P.C., Amendment in Reply to Non-Final Action of Jan. 27, 2010 in U.S. Appl. No. 10/964,888, filed Apr. 14, 2010, 15 pages.

USPTO Notice of Allowance in U.S. Appl. No. 10/964,888, mailed Jul. 20, 2010, 6 pages.

Fish & Richardson P.C., Response to Notice of Allowance of Jul. 20, 2010 in U.S. Appl. No. 10/964,888, filed Oct. 20, 2010, 3 pages.

Fish & Richardson P.C., Amendment in Reply to Action of May 25, 2010 in U.S. Appl. No. 12/167,614, filed Nov. 23, 2010, 28 pages.

USPTO Final Office Action in U.S. Appl. No. 12/167,614, mailed Jan. 24, 2011, 52 pages.

* cited by examiner

SEQUENCE LISTING

<160> NUMBER OF SEQ ID NOS: 22

<210> SEQ ID NO 1
<211> LENGTH: 492
<212> TYPE: DNA
<213> ORGANISM: Homo sapiens

<400> SEQUENCE: 1

| | | | | | |
|---|---|---|---|---|---|
| atgggcagca | cctgggggag | ccctggctgg | gtgcggctcg | ctctttgcct | gacgggctta | 60 |
| gtgctctcgc | tctacgcgct | gcacgtgaag | gcggcgcgcg | cccgggaccg | ggattaccgc | 120 |
| gcgctctgcg | acgtgggcac | cgccatcagc | tgttcgcgcg | tcttctcctc | caggtggggc | 180 |
| aggggtttcg | ggctggtgga | gcatgtgctg | gacaggaca | gcatcctcaa | tcaatccaac | 240 |
| agcatattcg | gttgcatctt | ctacacacta | cagctattgt | taggttgcct | gcggacacgc | 300 |
| tgggcctctg | tcctgatgct | gctgagctcc | ctggtgtctc | tcgctggttc | tgtctacctg | 360 |
| gcctggatcc | tgttcttcgt | gctctatgat | ttctgcattg | tttgtatcac | cacctatgct | 420 |
| atcaacgtga | gcctgatgtg | gctcagtttc | cggaaggtcc | aagaacccca | gggcaaggct | 480 |
| aagaggcact | ga | | | | | 492 |

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cacaccatgg ggcgcccact            20

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
gagtgggatc tcactttaat gga        23

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
caccatgggc agcacctggg gga        23

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gctcagtgcc tcttagcctt            20

<210> SEQ ID NO 6

<211> LENGTH: 9707
<212> TYPE: DNA
<213> ORGANISM: Artificial Sequence
<220> FEATURE:
<223> OTHER INFORMATION: Synthetic construct-F10nopA

<400> SEQUENCE: 6

| | | | | | |
|---|---|---|---|---|---|
| gacggatcgg | gagatctccc | gatccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagcttggta | ccgagctcgg | atccactagt | ccagtgtggt | ggaattctgc | 960 |
| agatcacacc | atggggcgcc | cactgcacct | cgtcctgctc | agtgcctccc | tggctggcct | 1020 |
| cctgctgctc | ggggaaagtc | tgttcatccg | cagggagcag | gccaacaaca | tcctggcgag | 1080 |
| ggtcacgagg | gccaattcct | ttcttgaaga | gatgaagaaa | ggacacctcg | aaagagagtg | 1140 |
| catggaagag | acctgctcat | acgaagaggc | ccgcgaggtc | tttgaggaca | gcgacaagac | 1200 |
| gaatgaattc | tggaataaat | acaaagatgg | cgaccagtgt | gagaccagtc | cttgccagaa | 1260 |
| ccagggcaaa | tgtaaagacg | gcctcgggga | atacacctgc | acctgtttag | aaggattcga | 1320 |
| aggcaaaaac | tgtgaattat | tcacacggaa | gctctgcagc | ctggacaacg | ggactgtga | 1380 |
| ccagttctgc | cacgaggaac | agaactctgt | ggtgtgctcc | tgcgcccgcg | ggtacaccct | 1440 |
| ggctgacaac | ggcaaggcct | gcattccac | agggccctac | cctgtgggga | acagacccct | 1500 |
| ggaacgcagg | aagaggtcag | tgcccaggc | caccagcagc | agcgggagg | ccctgacag | 1560 |
| catcacatgg | aagccatatg | atgcagccga | cctggaccc | accgagaacc | cttcgacct | 1620 |
| gcttgacttc | aaccagacgc | agcctgagag | gggcgacaac | aacctcacca | ggatcgtggg | 1680 |
| gggccaggaa | tgcaaggacg | gggagtgtcc | ctggcaggcc | ctgctcatca | atgaggaaaa | 1740 |
| cgagggtttc | tgtggtggaa | ccattctgag | cgagttctac | atcctaacgg | cagcccactg | 1800 |
| tctctaccaa | gccaagagat | tcaaggtgag | ggtaggggac | cggaacacgg | agcaggagga | 1860 |
| gggcggtgag | gcggtgcacg | aggtggaggt | ggtcatcaag | cacaaccggt | tcacaaagga | 1920 |
| gacctatgac | ttcgacatcg | ccgtgctccg | gctcaagacc | cccatcacct | tccgcatgaa | 1980 |
| cgtggcgcct | gcctgcctcc | ccgagcgtga | ctgggccgag | tccacgctga | tgacgcagaa | 2040 |
| gacggggatt | gtgagcggct | tcgggcgcac | ccacgagaag | ggccgccagt | ccaccaggct | 2100 |
| caagatgctg | gaggtgccct | acgtggaccg | caacagctgc | aagctgtcca | gcagcttcat | 2160 |

```
catcacccag aacatgttct gtgccggcta cgacaccaag caggaggatg cctgccaggg    2220
ggacagcggg ggcccgcacg tcacccgctt caaggacacc tacttcgtga caggcatcgt    2280
cagctgggga gagggctgtg cccgtaaggg gaagtacggg atctacacca aggtcaccgc    2340
cttcctcaag tggatcgaca ggtccatgaa accaggggc ttgcccaagg ccaagagcca    2400
tgccccggag gtcataacgt cctctccatt aaagtgagat cccactcatc cagcacagtg    2460
gcggccgctc gagtctagag ggcccgttta acccgctga tcagcctcga ctgtgccttc    2520
tagttgccag ccatctgttg tttgcccctc ccccgtgcct tccttgaccc tggaaggtgc    2580
cactcccact gtccttttcct aataaaatga ggaaattgca tcgcattgtc tgagtaggtg    2640
tcattctatt ctggggggtg gggtggggca ggacagcaag ggggaggatt gggaagacaa    2700
tagcaggcat gctgggatg cggtgggctc tatggcttct gaggcggaaa gaaccagctg    2760
gggctctagg gggtatcccc acgcgccctg tagcggcgca ttaagcgcgg cgggtgtggt    2820
ggttacgcgc agcgtgaccg ctacacttgc cagcgcccta cgcccgctc ctttcgcttt    2880 cttcccttcc tttctcgcca cgttcgccgg ctttccccgt caagctctaa atcgggggct    2940 cccttaggg ttccgattta gtgctttacg gcaccttcga ccccaaaaaa cttgattagg    3000
gctgtggaat gtgtgtcagt tagggtgtgg aaagtcccca ggctcccag caggcagaag    3060 tatgcaaagc atgcatctca attagtcagc aaccaggtgt ggaaagtccc caggctcccc    3120
agcaggcaga agtatgcaaa gcatgcatct caattagtca gcaaccatag tcccgcccct    3180
aactccgccc atcccgcccc taactccgcc cagttccgcc cattctccgc cccatggctg    3240
actaattttt tttatttatg cagaggccga ggccgcctcg gcctctgagc tattccagaa    3300
gtagtgagga ggcttttttg gaggcctagg cttttgcaaa aagctctctg gctaactaga    3360
gaacccactg cttactggct tatcgaaatt aatacgactc actataggga gacccaagct    3420
ggctagcgtt taaacttaag cttggtaccg agctcggatc cactagtcca gtgtggtgga    3480
attgcccttt ccgcagagca atggcggtgt ctgccgggtc cgcgcggacc tcgcccagct    3540
cagataaagt acagaaagac aaggctgaac tgatctcagg gcccaggcag acagccgaa    3600 tagggaaact cttgggtttt gagtggacag atttgtccag ttggcggagg ctggtgaccc    3660
tgctgaatcg accaacggac cctgcaagct tagctgtctt tcgttttctt tttgggttct    3720
tgatggtgct agacattccc caggagcggg ggctcagctc tctggaccgg aaataccttg    3780
atgggctgga tgtgtgccgc ttccccttgc tggatgccct acgcccactg ccacttgact    3840
ggatgtatct tgtctacacc atcatgtttc tgggggcact gggcatgatg ctgggcctgt    3900
gctaccggat aagctgtgtg ttattcctgc tgccatactg gtatgtgttt ctcctggaca    3960
agacatcatg aacaaccac tcctatctgt atgggttgtt ggccttcag ctaacattca    4020 tggatgcaaa ccactactgg tctgtggacg gtctgctgaa tgcccatagg aggaatgccc    4080 acgtgccct ttggaactat gcagtgctcc gtggccagat cttcattgtg tacttcattg    4140
cgggtgtgaa aaagctggat gcagactggg ttgaaggcta ttccatggaa tatttgtccc    4200
ggcactggct cttcagtccc ttcaaactgc tgttgtctga ggagctgact agcctgctgg    4260
tcgtgcactg gggtgggctg ctgcttgacc tctcagctgg tttcctgctc ttttttgatg    4320
tctcaagatc cattgcctg ttcttttgtgt cctacttcca ctgcatgaat tcccagcttt    4380
tcagcattgg tatgttctcc tacgtcatgc tggccagcag ccctctcttc tgctcccctg    4440
agtggcctcg gaagctggtg tcctactgcc ccgaaggtt gcaacaactg ttgccctca    4500 aggcagcccc tcagcccagt gtttcctgtg tgtataagag gagccggggc aaaagtggcc    4560
```

```
agaagccagg gctgcgccat cagctgggag ctgccttcac cctgctctac ctcctggagc    4620
agctattcct gccctattct cattttctca cccagggcta taacaactgg acaaatgggc    4680
tgtatggcta ttcctgggac atgatggtgc actcccgctc ccaccagcac gtgaagatca    4740
cctaccgtga tggccgcact ggcgaactgg gctaccttaa ccctgggta tttacacaga     4800 gtcggcgatg aaggatcat gcagacatgc tgaagcaata tgccacttgc ctgagccgcc    4860
tgcttcccaa gtataatgtc actgagcccc agatctactt tgatatttgg gtctccatca    4920
atgaccgctt ccagcagagg attttgacc ctcgtgtgga catcgtgcag gccgcttggt    4980 cacccttca gcgcacatcc tgggtgcaac cactcttgat ggacctgtct ccctggaggg    5040
ccaagttaca ggaaatcaag agcagcctag acaaccacac tgaggtggtc ttcattgcag    5100
atttccctgg actgcacttg gagaattttg tgagtgaaga cctgggcaac actagcatcc    5160
agctgctgca gggggaagtg actgtggagc ttgtggcaga acagaagaac cagactcttc    5220
gagagggaga aaaaatgcag ttgcctgctg gtgagtacca taaggtgtat acgacatcac    5280
ctagcccttc ttgctacatg tacgtctatg tcaacactac agagcttgca ctggagcaag    5340
acctggcata tctgcaagaa ttaaaggaaa aggtggagaa tggaagtgaa acagggcctc    5400
tacccccaga gctgcagcct ctgttggaag gggaagtaaa aggggggccct gagccaacac    5460 ctctggttca gacctttctt agacgccaac aaaggctcca ggagattgaa cgccggcgaa    5520
atactccttt ccatgagcga ttcttccgct tcttgttgcg aaagctctat gtctttcgcc    5580
gcagcttcct gatgacttgt atctcacttc gaaatctgat attaggccgt ccttccctgg    5640
agcagctggc ccaggaggtg acttatgcaa acttgagacc ctttgaggca gttggagaac    5700
tgaatccctc aaaacacggat tcttcacatt ctaatcctcc tgagtcaaat cctgatcctg    5760
tccactcaga gttctgaagg gggccagatg ttggaagggc aattcgagtc tagagggccc    5820
gccctgatag acggttttc gcccttgac gttggagtcc acgttcttta atagtggact    5880
cttgttccaa actggaacaa cactcaaccc tatctcggtc tattcttttg atttataagg    5940
gattttgccg atttcggcct attggttaaa aaatgagctg atttaacaaa aatttaacgc    6000
gaattaattc tgtggaatgt gtgtcagtta gggtgtggaa agtccccagg ctccccagca    6060
ggcagaagta tgcaaagcat gcatctcaat tagtcagcaa ccaggtgtgg aaagtcccca    6120
ggctccccag caggcagaag tatgcaaagc atgcatctca attagtcagc aaccatagtc    6180
ccgcccctaa ctccgcccat cccgccccta actccgccca gttccgccca ttctccgccc    6240
catggctgac taattttttt tatttatgca gaggccgagg ccgcctctgc ctctgagcta    6300
ttccagaagt agtgaggagg ctttttggga ggcctaggct tttgcaaaaa gctcccggga    6360
gcttgtatat ccattttcgg atctgatcaa gagacaggat gaggatcgtt tcgcatgatt    6420
gaacaagatg gattgcacgc aggttctccg gccgcttggg tggagaggct attcggctat    6480
gactgggcac aacagacaat cggctgctct gatgccgccg tgttccggct gtcagcgcag    6540
gggcgcccgg ttcttttgt caagaccgac ctgtccggtg ccctgaatga actgcaggac    6600
gaggcagcgc ggctatcgtg gctggccacg acgggcgttc cttgcgcagc tgtgctcgac    6660
gttgtcactg aagcgggaag ggactggctg ctattgggcg aagtgccggg gcaggatctc    6720
ctgtcatctc accttgctcc tgccgagaaa gtatccatca tggctgatgc aatgcggcgg    6780
ctgcatacgc ttgatccggc tacctgccca ttcgaccacc aagcgaaaca tcgcatcgag    6840
cgagcacgta ctcggatgga agccggtctt gtcgatcagg atgatctgga cgaagagcat    6900
caggggctcg cgccagccga actgttcgcc aggctcaagg cgcgcatgcc cgacggcgag    6960
```

```
gatctcgtcg tgacccatgg cgatgcctgc ttgccgaata tcatggtgga aaatggccgc    7020
ttttctggat tcatcgactg tggccggctg ggtgtggcgg accgctatca ggacatagcg    7080
ttggctaccc gtgatattgc tgaagagctt ggcggcgaat gggctgaccg cttcctcgtg    7140
ctttacggta tcgccgctcc cgattcgcag cgcatcgcct tctatcgcct tcttgacgag    7200
ttcttctgag cgggactctg gggttcgaaa tgaccgacca agcgacgccc aacctgccat    7260
cacgagattt cgattccacc gccgccttct atgaaaggtt gggcttcgga atcgttttcc    7320
gggacgccgg ctggatgatc ctccagcgcg gggatctcat gctggagttc ttcgcccacc    7380
ccaacttgtt tattgcagct tataatggtt acaaataaag caatagcatc acaaatttca    7440
caaataaagc atttttttca ctgcattcta gttgtggttt gtccaaactc atcaatgtat    7500
cttatcatgt ctgtataccg tcgacctcta gctagagctt ggcgtaatca tggtcatagc    7560
tgtttcctgt gtgaaattgt tatccgctca caattccaca acatacga gccggaagca     7620
taaagtgtaa agcctggggt gcctaatgag tgagctaact cacattaatt gcgttgcgct    7680
cactgcccgc tttccagtcg ggaaacctgt cgtgccagct gcattaatga atcggccaac    7740
gcgcggggag aggcggtttg cgtattgggc gctcttccgc ttcctcgctc actgactcgc    7800
tgcgctcggt cgttcggctg cggcgagcgg tatcagctca ctcaaaggcg gtaatacggt    7860
tatccacaga atcaggggat aacgcaggaa agaacatgtg agcaaaaggc cagcaaaagg    7920
ccaggaaccg taaaaaggcc gcgttgctgg cgttttttcca taggctccgc cccctgacg   7980
agcatcacaa aaatcgacgc tcaagtcaga ggtggcgaaa cccgacagga ctataaagat    8040
accaggcgtt ccccctgga agctccctcg tgcgctctcc tgttccgacc ctgccgctta    8100
ccggatacct gtccgccttt ctcccttcgg aagcgtggc gctttctcat agctcacgct    8160
gtaggtatct cagttcggtg taggtcgttc gctccaagct gggctgtgtg cacgaacccc    8220
ccgttcagcc cgaccgctgc gccttatccg gtaactatcg tcttgagtcc aacccggtaa    8280
gacacgactt atcgccactg gcagcagcca ctggtaacag gattagcaga gcgaggtatg    8340
taggcggtgc tacagagttc ttgaagtggt ggcctaacta cggctacact agaagaacag    8400
tatttggtat ctgcgctctg ctgaagccag ttaccttcgg aaaaagagtt ggtagctctt    8460
gatccggcaa acaaaccacc gctggtagcg gttttttttgt ttgcaagcag cagattacgc    8520
gcagaaaaaa aggatctcaa gaagatcctt tgatcttttc tacggggtct gacgctcagt    8580
ggaacgaaaa ctcacgttaa gggattttgg tcatgagatt atcaaaaagg atcttcacct    8640
agatccttt aaattaaaaa tgaagtttta atcaatcta aagtatatat gagtaaactt      8700
ggtctgacag ttaccaatgc ttaatcagtg aggcacctat ctcagcgatc tgtctatttc    8760
gttcatccat agttgcctga ctccccgtcg tgtagataac tacgatacgg gagggcttac    8820
catctggccc cagtgctgca atgataccgc gagacccacg ctcaccggct ccagatttat    8880
cagcaataaa ccagccagcc ggaagggccg agcgcagaag tggtcctgca actttatccg    8940
cctccatcca gtctattaat tgttgccggg aagctagagt aagtagttcg ccagttaata    9000
gtttgcgcaa cgttgttgcc attgctacag gcatcgtggt gtcacgctcg tcgtttggta    9060
tggcttcatt cagctccggt tcccaacgat caaggcgagt tacatgatcc cccatgttgt    9120
gcaaaaaagc ggttagctcc ttcggtcctc cgatcgttgt cagaagtaag ttggccgcag    9180
tgttatcact catggttatg gcagcactgc ataattctct tactgtcatg ccatccgtaa    9240
gatgcttttc tgtgactggt gagtactcaa ccaagtcatt ctgagaatag tgtatgcggc    9300
gaccgagttg ctcttgcccg gcgtcaatac gggataatac cgcgccacat agcagaactt    9360
```

| | |
|---|---|
| taaaagtgct catcattgga aaacgttctt cggggcgaaa actctcaagg atcttaccgc | 9420 |
| tgttgagatc cagttcgatg taacccactc gtgcacccaa ctgatcttca gcatctttta | 9480 |
| ctttcaccag cgtttctggg tgagcaaaaa caggaaggca aaatgccgca aaaagggaa | 9540 |
| taagggcgac acgaaatgt tgaatactca tactcttcct ttttcaatat tattgaagca | 9600 |
| tttatcaggg ttattgtctc atgagcggat acatatttga atgtatttag aaaaataaac | 9660 |
| aaatagggt tccgcgcaca tttccccgaa aagtgccacc tgacgtc | 9707 |

<210> SEQ ID NO 7
<211> LENGTH: 4029
<212> TYPE: DNA
<213> ORGANISM: Artificial Sequence
<220> FEATURE:
<223> OTHER INFORMATION: Synthetic construct-VKOR zeo

<400> SEQUENCE: 7

| | |
|---|---|
| ggatcgatcc ggctgtggaa tgtgtgtcag ttagggtgtg aaagtcccca ggctccccca | 60 |
| gcaggcagaa gtatgcaaag catgcatctc aattagtcag caaccaggtg tggaaagtcc | 120 |
| ccaggctccc cagcaggcag aagtatgcaa agcatgcatc tcaattagtc agcaaccata | 180 |
| gtcccgcccc taactccgcc catcccgccc ctaactccgc ccagttccgc ccattctccg | 240 |
| ccccatggct gactaatttt ttttatttat gcagaggccg aggccgcctc ggcctctgag | 300 |
| ctattccaga agtagtgagg aggcttttt ggaggcctag gcttttgcaa aaagctctct | 360 |
| ggctaactag agaacccact gcttactggc ttatcgaaat taatacgact cactataggg | 420 |
| agacccaagc tggctagcgt ttaaacttaa gcttggtacc gagctcggat ccactagtcc | 480 |
| agtgtggtgg aattgcccct tcaccatggg agcacctggg ggagccctgg ctgggtgcgg | 540 |
| ctcgctcttt gcctgacggg cttagtgctc tcgctctacg cgctgcacgt gaaggcggcg | 600 |
| cgcgcccggg accgggatta ccgcgcgctc tgcgacgtgg gcaccgccat cagctgttcg | 660 |
| cgcgtcttct cctccaggtg gggcagggt ttcgggctgg tggagcatgt gctgggacag | 720 |
| gacagcatcc tcaatcaatc caacagcata ttcggttgca tcttctacac actacagcta | 780 |
| tgttaggtt gcctgcggac acgctgggcc tctgtcctga tgctgctgag ctccctggtg | 840 |
| tctctcgctg gttctgtcta cctggcctgg atcctgttct tcgtgctcta tgatttctgc | 900 |
| attgtttgta tcaccaccta tgctatcaac gtgagcctga tgtggctcag tttccggaag | 960 |
| gtccaagaac cccagggcaa ggctaagagg cactgaacaa gggcaattct gcagatatcc | 1020 |
| agcacagtgg cggccgctcg agtctagagg gcccgtttaa acccgctgat cagcctcgac | 1080 |
| tgtgccttct agttgccagc catctgttgt ttgcccctcc ccgtgccttc cttgaccct | 1140 |
| ggaaggtgcc actcccactg tccttttccta ataaaatgag gaaattgcat cgcattgtct | 1200 |
| gagtaggtgt cattctattc tggggggtgg ggtggggcag gacagcaagg ggaggattg | 1260 |
| ggaagacaat agcaggcatg ctggggatgc ggtgggctct atggcttctg aggcggaaag | 1320 |
| aaccagcatg tgagcaaaag ccagcaaaa ggccaggaac cgtaaaaagg ccgcgttgct | 1380 |
| ggcgttttc cataggctcc gccccctga cgagcatcac aaaaatcgac gctcaagtca | 1440 |
| gaggtggcga aacccgacag gactataaag ataccaggcg tttccccctg gaagctccct | 1500 |
| cgtgcgctct cctgttccga ccctgccgct taccggatac ctgtccgcct ttctcccttc | 1560 |
| gggaagcgtg gcgctttctc atagctcacg ctgtaggtat ctcagttcgg tgtaggtcgt | 1620 |
| tcgctccaag ctgggctgtg tgcacgaacc cccgttcag cccgaccgct gcgccttatc | 1680 |
| cggtaactat cgtcttgagt ccaacccggt aagacacgac ttatcgccac tggcagcagc | 1740 |

```
cactggtaac aggattagca gagcgaggta tgtaggcggt gctacagagt tcttgaagtg   1800
gtggcctaac tacggctaca ctagaagaac agtatttggt atctgcgctc tgctgaagcc   1860
agttaccttc ggaaaaagag ttggtagctc ttgatccggc aaacaaacca ccgctggtag   1920
cggtggtttt tttgtttgca agcagcagat tacgcgcaga aaaaaaggat ctcaagaaga   1980
tcctttgatc ttttctacgg ggtctgacgc tcagtggaac gaaaactcac gttaagggat   2040
tttggtcatg acattaacct ataaaaatag gcgtatcacg aggccctttc gtctcgcgcg   2100
tttcggtgat gacggtgaaa acctctgaca catgcagctc ccggagacgg tcacagcttg   2160
tctgtaagcg gatgccggga gcagacaagc ccgtcagggc gcgtcagcgg gtgttggcgg   2220
gtgtcgggc tggcttaact atgcggcatc agagcagatt gtactgagag tgcaccatat   2280
gcggtgtgaa ataccgcaca gatgcgtaag gagaaaatac cgcatcagga cgcgccctgt   2340
agcggcgcat taagcgcggc gggtgtggtg gttacgcgca gcgtgaccgc tacacttgcc   2400
agcgccctag cgcccgctcc tttcgctttc ttcccttcct ttctcgccac gttcgccggc   2460
tttccccgtc aagctctaaa tcgggggctc cctttagggt tccgatttag tgctttacgg   2520
cacctcgacc ccaaaaaact tgattagggt gatggttcac gtagtgggcc atcgccctga   2580
tagacggttt ttcgcccttt gacgttggag tccacgttct ttaatagtgg actcttgttc   2640
caaactggaa caacactcaa ccctatctcg gtctattctt ttgatttata agggattttg   2700
ccgatttcgg cctattggtt aaaaaatgag ctgatttaac aaaaatttaa cgcgaatttt   2760
aacaaaatat taacgcttac aatttccatt cgccattcag gctgaactag atctagagtc   2820
cgttacataa cttacggtaa atggcccgcc tggctgaccg cccaacgacc cccgcccatt   2880
gacgtcaata atgacgtatg ttcccatagt aacgccaata gggactttcc attgacgtca   2940
atgggtggag tatttacggt aaactgccca cttggcagta catcaagtgt atcatatgcc   3000
aagtacgccc cctattgacg tcaatgacgg taaatggccc gcctggcatt atgcccagta   3060
catgacctta tgggactttc ctacttggca gtacatctac gtattagtca tcgctattac   3120
catggtgatg cggttttggc agtacatcaa tgggcgtgga tagcggtttg actcacgggg   3180
atttccaagt ctccacccca ttgacgtcaa tgggagtttg ttttggcacc aaaatcaacg   3240
ggactttcca aaatgtcgta acaactccgc cccattgacg caaatgggcg gtaggcgtgt   3300
acggtgggag gtctatataa gcagagctcg tttagtgaac cgtcagatcg cctggagacg   3360
ccatccacgc tgttttgacc tccatagaag acaccgggac cgatccagcc tccgcggccg   3420
ggaacggtgc attggaacgg accgtgttga caattaatca tcggcatagt atatcggcat   3480
agtataatac gacaaggtga ggaactaaac catggccaag ttgaccagtg ccgttccggt   3540
gctcaccgcg cgcgacgtcg ccggagcggt cgagttctgg accgaccggc tcgggttctc   3600
ccgggacttc gtggaggacg acttcgccgg tgtggtccgg gacgacgtga ccctgttcat   3660
cagcgcggtc caggaccagg tggtgccgga caacaccctg gcctgggtgt gggtgcgcgg   3720
cctggacgag ctgtacgccg agtggtcgga ggtcgtgtcc acgaacttcc gggacgcctc   3780
cgggccggcc atgaccgaga tcggcgagca gccgtgggg cggagttcg ccctgcgcga   3840
cccggccggc aactgcgtgc acttcgtggc cgaggagcag gactgacact cgacctcgaa   3900
acttgtttat tgcagcttat aatggttaca aataaagcaa tagcatcaca aatttcacaa   3960
ataaagcatt ttttcactg cattctagtt gtggtttgtc caaactcatc aatgtatctt   4020
atcatgtct                                                            4029
```

<210> SEQ ID NO 8

```
<211> LENGTH: 24
<212> TYPE: DNA
<213> ORGANISM: Artificial Sequence
<220> FEATURE:
<223> OTHER INFORMATION: Primer

<400> SEQUENCE: 8
acacctctgg ttcagacctt tctt                                               24

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
aatcgctcat ggaaaggagt attt                                               24

<210> SEQ ID NO 10
<211> LENGTH: 27
<212> TYPE: DNA
<213> ORGANISM: Artificial Sequence
<220> FEATURE:
<223> OTHER INFORMATION: Probe sequence

<400> SEQUENCE: 10
caacaaaggc tccaggagat tgaacgc                                            27

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
ccgcaacagc tgcaagct                                                      18

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
tgtcgtagcc ggcacaga                                                      18

<210> SEQ ID NO 13
<211> LENGTH: 28
<212> TYPE: DNA
<213> ORGANISM: Artificial Sequence
<220> FEATURE:
<223> OTHER INFORMATION: Probe sequence

<400> SEQUENCE: 13
cagcagcttc atcatcaccc agaacatg                                           28

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
```

```
gctgggcctc tgtcctgat                                                  19
```

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15

```
atccaggcca ggtagacaga ac                                              22
```

<210> SEQ ID NO 16
<211> LENGTH: 25
<212> TYPE: DNA
<213> ORGANISM: Artificial Sequence
<220> FEATURE:
<223> OTHER INFORMATION: Probe sequence

<400> SEQUENCE: 16

```
ctgctgagct ccctggtgtc tctcg                                           25
```

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17

```
tggaggacaa aaccgaaaga ga                                              22
```

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18

```
catccgagcc ctccacaa                                                   18
```

<210> SEQ ID NO 19
<211> LENGTH: 25
<212> TYPE: DNA
<213> ORGANISM: Artificial Sequence
<220> FEATURE:
<223> OTHER INFORMATION: Probe sequence

<400> SEQUENCE: 19

```
ctcctggaat cctacatcga cgggc                                           25
```

<210> SEQ ID NO 20
<211> LENGTH: 10238
<212> TYPE: DNA
<213> ORGANISM: Artificial Sequence
<220> FEATURE:
<223> OTHER INFORMATION: Synthetic construct-PP6

<400> SEQUENCE: 20

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
```

```
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattgccc    960
ttattcctca gtgacccagg agctgacaca ctatggcgca cgtccgaggc ttgcagctgc   1020
ctggctgcct ggccctggct gccctgtgta gccttgtgca cagccagcat gtgttcctgg   1080
ctcctcagca agcacggtcg ctgctccagc gggtccggcg agccaacacc ttcttggagg   1140
aggtgcgcaa gggcaacctg gagcgagagt gcgtggagga cgtgcagc tacgaggagg   1200 ccttcgaggc tctggagtcc tccacggcta cggatgtgtt ctgggccaag tacacagctt   1260
gtgagacagc gaggacgcct cgagataagc ttgctgcatg tctggaaggt aactgtgctg   1320
agggtctggg tacgaactac cgagggcatg tgaacatcac ccggtcaggc attgagtgcc   1380
agctatggag gagtcgctac ccacataagc ctgaaatcaa ctccactacc catcctgggg   1440
ccgacctaca ggagaatttc tgccgcaacc ccgacagcag caccacggga ccctggtgct   1500
acactacaga ccccaccgtg aggaggcagg aatgcagcat ccctgtctgt ggccaggatc   1560
aagtcactgt agcgatgact ccacgctccg aaggctccag tgtgaatctg tcacctccat   1620
tggagcagtg tgtccctgat cgggggcagc agtaccaggg gcgcctggcg gtgaccacac   1680
atgggctccc ctgcctggcc tgggccacg cacaggccaa ggccctgagc aagcaccagg   1740
acttcaactc agctgtgcag ctggtggaga acttctgccg caacccagac ggggatgagg   1800
agggcgtgtg gtgctatgtg gccgggaagc ctggcgactt tgggtactgc gacctcaact   1860
attgtgagga ggccgtggag gaggagacag gagatgggct ggatgaggac tcagacaggg   1920
ccatcgaagg gcgtaccgcc accagtgagt accagacttt cttcaatccg aggacctttg   1980
gctcgggaga ggcagactgt gggctgcgac ctctgttcga gaagaagtcg ctggaggaca   2040
aaaccgaaag agagctcctg gaatcctaca tcgacgggcg cattgtggag ggctcggatg   2100
cagagatcgg catgtcacct tggcaggtga tgctttttcg gaagagtccc caggagctgc   2160
tgtgtggggc cagcctcatc agtgaccgct gggtcctcac cgccgcccac tgcctcctgt   2220
acccgcccct ggacaagaac ttcaccgaga atgaccttct ggtgcgcatt ggcaagcact   2280
cccgcaccag gtacgagcga aacattgaaa agatatccat gttggaaaag atctacatcc   2340 accccagta caactggcgg gagaacctgg accgggacat tgccctgatg aagctgaaga   2400
agcctgttgc cttcagtgac tacattcacc ctgtgtgtct gcccgacagg gagacggcag   2460
ccagcttgct ccaggctgga tacaaggggc gggtgacagg ctggggcaac ctgaaggaga   2520
cgtggacagc caacgttggt aaggggcagc ccagtgtcct gcaggtggtg aacctgccca   2580
ttgtggagcg gccggtctgc aaggactcca cccggatccg catcactgac aacatgttct   2640
```

```
gtgctggtta caagcctgat gaagggaaac gaggggatgc ctgtgaaggt gacagtgggg    2700
gaccctttgt catgaagagc ccctttaaca accgctggta tcaaatgggc atcgtctcat    2760
ggggtgaagg ctgtgaccgg gatgggaaat atggcttcta cacacatgtg ttccgcctga    2820
agaagtggat acagaaggtc attgatcagt ttggagagta gaagggcaat tctgcagata    2880
tccagcacag tggcggccgc tcggttccta gagggcccgt ttaaaccccgc tgatcagcct    2940 cgactgtgcc ttctagttgc cagccatctg ttgtttgccc ctccccgtg ccttccttga    3000 ccctggaagg tgccactccc actgtccttt cctaataaaa tgaggaaatt gcatcgcatt    3060
gtctgagtag gtgtcattct attctggggg gtggggtggg gcaggacagc aagggggagg    3120
attgggaaga caatagcagg catgctgggg atgcggtggg ctctatggct tctgaggcgg    3180
aaagaaccag ctggggctct agggggtatc cccacgcgcc ctgtagcggc gcattaagcg    3240
cggcgggtgt ggtggttacg cgcagcgtga ccgctacact tgccagcgcc ctagcgcccg    3300 ctccttttcgc tttcttccct tcctttctcg ccacgttcgc cggctttccc cgtcaagctc    3360
taaatcgggg gctccctta gggttccgat ttagtgcttt acggcacctc gaccccaaaa    3420
aacttgatta gggtgatggt tcacatcgat gcaatttcct cattttatta ggaaaggaca    3480
gtgggagtgg caccttccag ggtcaaggaa ggcacggggg aggggcaaac aacagatggc    3540
tggcaactag aaggcacagt cgaggctgat cagcgggttt aaacgggccc tctagactcg    3600 aattgcccctt ccaacatctg gcccccttca gaactctgag tggacaggat caggatttga    3660
ctcaggagga ttagaatgtg aagaatccgt gtttgaggga ttcagttctc caactgcctc    3720
aaagggtctc aagtttgcat aagtcacctc ctgggccagc tgctccaggg aaggacggcc    3780
taatatcaga tttcgaagtg agatacaagt catcaggaag ctgcggcgaa agacatagag    3840
ctttcgcaac aagaagcgga agaatcgctc atggaaagga gtatttcgcc ggcgttcaat    3900
ctcctggagc ctttgttggc gtctaagaaa ggtctgaacc agaggtgttg gctcagggcc    3960
cccttttact tccccttcca acagaggctg cagctctggg ggtagaggcc ctgtttcact    4020
tccattctcc acctttttcct ttaattcttg cagatatgcc aggtcttgct ccagtgcaag    4080
ctctgtagtg ttgacataga cgtacatgta gcaagaaggg ctaggtgatg tcgtatacac    4140
cttatggtac tcaccagcag gcaactgcat ttttttctccc tctcgaagag tctggttctt    4200
ctgttctgcc acaagctcca cagtcacttc ccccctgcagc agctggatgc tagtgttgcc    4260
caggtcttca ctcacaaaat tctccaagtg cagtccaggg aaatctgcaa tgaagaccac    4320
ctcagtgtgg ttgtctaggc tgctcttgat ttcctgtaac ttggccctcc agggagacag    4380
gtccatcaag agtggttgca cccaggatgt gcgctgaaag ggtgaccaag cggcctgcac    4440
gatgtccaca cgagggtcaa aaatcctctg ctggaagcgg tcattgatgg agacccaaat    4500
atcaaagtag atctggggct cagtgacatt atacttggga agcaggcggc tcaggcaagt    4560
ggcatattgc ttcagcatgt ctgcatgatc cttccatcgc cgactctgtg taaatacccc    4620
agggttaagg tagcccagtt cgccagtgcg gccatcacgg taggtgatct tcacgtgctg    4680
gtgggagcgg gagtgcacca tcatgtccca ggaatagcca tacagcccat tgtccagtt    4740 gttatagccc tgggtgagaa aatgagaata gggcaggaat agctgctcca ggaggtagag    4800
cagggtgaag gcagctccca gctgatgcg cagccctggc ttctggccac ttttgccccg    4860 gctcctcttta tacacacagg aaacactggg ctgagggggct gccttgaggg gcaacagttg    4920
ttgcaacctt cggggggcagt aggacaccag cttccgaggc cactcagggg agcagaagag    4980
agggctgctg gccagcatga cgtaggagaa cataccaatg ctgaaaagct gggaattcat    5040
```

```
gcagtggaag taggacacaa agaacaggcc aatggatctt gagacatcaa aaaagagcag   5100
gaaaccagct gagaggtcaa gcagcagccc accccagtgc acgaccagca ggctagtcag   5160
ctcctcagac aacagcagtt tgaagggact gaagagccag tgccgggaca atattccat    5220 ggaatagcct tcaacccagt ctgcatccag cttttcaca cccgcaatga agtacacaat    5280
gaagatctgg ccacggagca ctgcatagtt ccaaggggc acgtgggcat tcctcctatg    5340
ggcattcagc agaccgtcca cagaccagta gtggtttgca tccatgaatg ttagctgaaa   5400
ggccaacaac ccatacagat aggagtggtt gttccatgat gtcttgtcca ggagaaacac   5460
ataccagtat ggcagcagga ataacacaca gcttatccgg tagcacaggc ccagcatcat   5520
gcccagtgcc cccagaaaca tgatggtgta gacaagatac atccagtcaa gtggcagtgg   5580
gcgtagggca tccagcaagg ggaagcggca cacatccagc ccatcaaggt atttccggtc   5640
cagagagctg agccccgct cctggggaat gtctagcacc atcaagaacc caaaagaaa     5700 acgaaagaca gctaagcttg cagggtccgt tggtcgattc agcagggtca ccagcctccg   5760
ccaactggac aaatctgtcc actcaaaacc caagagtttc cctattcggc tgtcctgcct   5820
gggccctgag atcagttcag ccttgtcttt ctgtacttta tctgagctgg gcgaggtccg   5880
cgcggacccg gcagacaccg ccattgctct gcggaaaggg caattccacc acactggact   5940
agtggatccg agctcggtac caagcttaag tttaaacgct agccagcttg ggtctcccta   6000
tagtgagtcg tattaatttc gataagccag taagcagtgg gttctctagt tagccagaga   6060 gcttttgca aaagcctagg cctccaaaaa agcctcctca ctacttctgg aatagctcag    6120
aggccgaggc ggcctcggcc tctgcataaa taaaaaaat tagtcagcca tggggcggag     6180
aatgggcgga actgggcgga gttaggggcg ggatgggcgg agttaggggc gggactatgg    6240
ttgctgacta attgagatgc atgctttgca tacttctgcc tgctggggag cctggggact    6300
ttccacaccc taactgacac acattccaca gccggatcga tgtgggccat cgccctgata    6360
gacggttttt cgccctttga cgttggagtc acgttctttt aatagtggac tcttgttcca    6420
aactggaaca acactcaacc ctatctcggt ctattctttt gatttataag gattttgcc     6480 gatttcggcc tattggttaa aaaatgagct gatttaacaa aatttaacg cgaattaatt     6540 ctgtggaatg tgtgtcagtt agggtgtgga aagtccccag gctccccagc aggcagaagt    6600
atgcaaagca tgcatctcaa ttagtcagca accaggtgtg aaagtccccc aggctcccca    6660
gcaggcagaa gtatgcaaag catgcatctc aattagtcag caaccatagt cccgccccta    6720
actccgccca tcccgcccct aactccgccc agttccgccc attctccgcc ccatggctga    6780
ctaatttttt ttatttatgc agaggccgag gccgcctctg cctctgagct attccagaag    6840
tagtgaggag gcttttttgg aggcctaggc ttttgcaaaa agctcccggg agcttgtata    6900 tccatttcg gatctgatca agagacagga tgaggatcgt ttcgcatgat tgaacaagat     6960
ggattgcacg caggttctcc ggccgcttgg gtggagaggc tattcggcta tgactgggca    7020
caacagacaa tcggctgctc tgatgccgcc gtgttccggc tgtcagcgca ggggcgcccg    7080 gttcttttg tcaagaccga cctgtccggt gccctgaatg aactgcagga cgaggcagcg     7140
cggctatcgt ggctggccac gacgggcgtt ccttgcgcag ctgtgctcga cgttgtcact    7200
gaagcgggaa gggactggct gctattgggc gaagtgccgg ggcaggatct cctgtcatct    7260
caccttgctc ctgccgagaa agtatccatc atggctgatg caatgcggcg gctgcatacg    7320
cttgatccgg ctacctgccc attcgaccac caagcgaaac atcgcatcga gcgagcacgt    7380
actcggatgg aagccggtct tgtcgatcag gatgatctgg acgaagagca tcaggggctc    7440
```

```
gcgccagccg aactgttcgc caggctcaag gcgcgcatgc ccgacggcga ggatctcgtc    7500
gtgacccatg gcgatgcctg cttgccgaat atcatggtgg aaaatggccg cttttctgga    7560
ttcatcgact gtggccggct gggtgtggcg gaccgctatc aggacatagc gttggctacc    7620
cgtgatattg ctgaagagct tggcggcgaa tgggctgacc gcttcctcgt gctttacggt    7680
atcgccgctc ccgattcgca gcgcatcgcc ttctatcgcc ttcttgacga gttcttctga    7740
gcgggactct ggggttcgaa atgaccgacc aagcgacgcc caacctgcca tcacgagatt    7800
tcgattccac cgccgccttc tatgaaaggt tgggcttcgg aatcgttttc cgggacgccg    7860
gctggatgat cctccagcgc ggggatctca tgctggagtt cttcgcccac ccaaacttgt    7920
ttattgcagc ttataatggt tacaaataaa gcaatagcat cacaaatttc acaaataaag    7980
catttttttc actgcattct agttgtggtt tgtccaaact catcaatgta tcttatcatg    8040
tctgtatacc gtcgacctct agctagagct tggcgtaatc atggtcatag ctgtttcctg    8100
tgtgaaattg ttatccgctc acaattccac acaacatacg agccgaagc ataaagtgta    8160 aagcctgggg tgcctaatga gtgagctaac tcacattaat tgcgttgcgc tcactgcccg    8220
ctttccagtc gggaaacctg tcgtgccagc tgcattaatg aatcggccaa cgcgcgggga    8280
gaggcggttt gcgtattggg cgctcttccg cttcctcgct cactgactcg ctgcgctcgg    8340
tcgttcggct gcggcgagcg gtatcagctc actcaaaggc ggtaatacgg ttatccacag    8400
aatcagggga taacgcagga aagaacatgt gagcaaaagg ccagcaaaag gccaggaacc    8460
gtaaaaaggc cgcgttgctg cgttttttcc ataggctccg ccccctgac gagcatcaca    8520 aaaatcgacg ctcaagtcag aggtggcgaa acccgacagg actataaaga taccaggcgt    8580
ttccccctgg aagctccctc gtgcgctctc ctgttccgac cctgccgctt accggatacc    8640
tgtccgcctt tctcccttcg ggaagcgtgg cgctttctca tagctcacgc tgtaggtatc    8700
tcagttcggt gtaggtcgtt cgctccaagc tgggctgtgt gcacgaaccc cccgttcagc    8760
ccgaccgctg cgccttatcc ggtaactatc gtcttgagtc caacccggta agacacgact    8820
tatcgccact ggcagcagcc actggtaaca ggattagcag agcgaggtat gtaggcggtg    8880
ctacagagtt cttgaagtgg tggcctaact acggctacac tagaagaaca gtatttggta    8940
tctgcgctct gctgaagcca gttaccttcg gaaaaagagt tggtagctct tgatccggca    9000
aacaaaccac cgctggtagc ggttttttg tttgcaagca gcagattacg cgcagaaaaa    9060
aaggatctca agaagatcct ttgatctttt ctacggggtc tgacgctcag tggaacgaaa    9120
actcacgtta agggattttg gtcatgagat tatcaaaaag gatcttcacc tagatccttt    9180
taaattaaaa atgaagtttt aaatcaatct aaagtatata tgagtaaact tggtctgaca    9240
gttaccaatg cttaatcagt gaggcaccta tctcagcgat ctgtctattt cgttcatcca    9300
tagttgcctg actccccgtc gtgtagataa ctacgatacg ggagggctta ccatctggcc    9360
ccagtgctgc aatgataccg cgagacccac gctcaccggc tccagattta tcagcaataa    9420
accagccagc cggaagggcc gagcgcagaa gtggtcctgc aactttatcc gcctccatcc    9480
agtctattaa ttgttgccgg gaagctgag taagtagttc gccagttaat agtttgcgca    9540
acgttgttgc cattgctaca ggcatcgtgg tgtcacgctc gtcgtttggt atggcttcat    9600
tcagctccgg ttcccaacga tcaaggcgag ttacatgatc ccccatgttg tgcaaaaaag    9660
cggttagctc cttcggtcct ccgatcgttg tcagaagtaa gttggccgca gtgttatcac    9720
tcatggttat ggcagcactg cataattctc ttactgtcat gccatccgta agatgctttt    9780
ctgtgactgg tgagtactca accaagtcat tctgagaata gtgtatgcgg cgaccgagtt    9840
```

```
gctcttgccc ggcgtcaata cgggataata ccgcgccaca tagcagaact ttaaaagtgc    9900
tcatcattgg aaaacgttct tcggggcgaa aactctcaag gatcttaccg ctgttgagat    9960
ccagttcgat gtaacccact cgtgcaccca actgatcttc agcatctttt actttcacca   10020
gcgtttctgg gtgagcaaaa acaggaaggc aaaatgccgc aaaaaaggga ataagggcga   10080
cacggaaatg ttgaatactc atactcttcc ttttcaata ttattgaagc atttatcagg    10140
gttattgtct catgagcgga tacatatttg aatgtattta gaaaaataaa caaatagggg   10200
ttccgcgcac atttccccga aaagtgccac ctgacgtc                           10238
```

<210> SEQ ID NO 21
<211> LENGTH: 10139
<212> TYPE: DNA
<213> ORGANISM: Artificial Sequence
<220> FEATURE:
<223> OTHER INFORMATION: Synthetic construct-PN32

<400> SEQUENCE: 21

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgc cccattgacg caaatgggcg      780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactagt ccagtgtggt ggaattgccc     960
ttattcctca gtgacccagg agctgacaca ctatggcgca cgtccgaggc ttgcagctgc    1020
ctggctgcct ggccctggct gccctgtgta gccttgtgca cagccagcat gtgttcctgg    1080
ctcctcagca agcacggtcg ctgctccagc gggtccggcg agccaacacc ttcttggagg    1140
aggtgcgcaa gggcaacctg gagcgagagt gcgtggagga cgtgcagc tacgaggagg      1200 ccttcgaggc tctggagtcc tccacggcta cggatgtgtt ctgggccaag tacacagctt    1260
gtgagacagc gaggacgcct cgagataagc ttgctgcatg tctggaaggt aactgtgctg    1320
agggtctggg tacgaactac cgagggcatg tgaacatcac ccggtcaggc attgagtgcc    1380
agctatggag gagtcgctac ccacataagc ctgaaatcaa ctccactacc catcctgggg    1440
ccgacctaca ggagaatttc tgccgcaacc ccgacagcag caccgggga ccctggtgct     1500 acactacaga ccccaccgtg aggaggcagg aatgcagcat ccctgtctgt ggccaggatc    1560
aagtcactgt agcgatgact ccacgctccg aaggctccag tgtgaatctg tcacctccat    1620
tggagcagtg tgtccctgat cgggggcagc agtaccaggg gcgcctggcg gtgaccacac    1680
```

```
atgggctccc ctgcctggcc tgggccagcg cacaggccaa ggccctgagc aagcaccagg    1740
acttcaactc agctgtgcag ctggtggaga acttctgccg caacccagac ggggatgagg    1800
agggcgtgtg gtgctatgtg gccgggaagc ctggcgactt tgggtactgc gacctcaact    1860
attgtgagga ggccgtggag gaggagacag gagatgggct ggatgaggac tcagacaggg    1920
ccatcgaagg gcgtaccgcc accagtgagt accagacttt cttcaatccg aggacctttg    1980
gctcgggaga ggcagactgt gggctgcgac ctctgttcga gaagaagtcg ctggaggaca    2040
aaaccgaaag agagctcctg gaatcctaca tcgacgggcg cattgtggag ggctcggatg    2100
cagagatcgg catgtcacct tggcaggtga tgcttttccg gaagagtccc caggagctgc    2160
tgtgtggggc cagcctcatc agtgaccgct gggtcctcac cgccgcccac tgcctcctgt    2220
acccgccctg gacaagaac  ttcaccgaga atgaccttct ggtgcgcatt ggcaagcact    2280
cccgcaccag gtacgagcga aacattgaaa agatatccat gttggaaaag atctacatcc    2340
accccaggta caactggcgg gagaacctgg accgggacat tgccctgatg aagctgaaga    2400
agcctgttgc cttcagtgac tacattcacc ctgtgtgtct gcccgacagg gagacggcag    2460
ccagcttgct ccaggctgga tacaagggc  gggtgacagg ctgggcaac  ctgaaggaga    2520 cgtggacagc caacgttggt aagggcagc  ccagtgtcct gcaggtggtg aacctgccca    2580
ttgtggagcg gccggtctgc aaggactcca cccggatccg catcactgac aacatgttct    2640
gtgctggtta caagcctgat gaagggaaac gaggggatgc ctgtgaaggt gacagtgggg    2700 gacccttgt  catgaagagc cccttaaca  accgctggta tcaaatgggc atcgtctcat    2760
ggggtgaagg ctgtgaccgg gatggaaat  atggcttcta cacacatgtg ttccgcctga    2820
agaagtggat acagaaggtc attgatcagt ttggagagta aagggcaat  tctgcagata    2880 tccagcacag tggcggccgc tcgagtctag agggcccgtt taaacccgct gatcagcctc    2940
gactgtgcct tctagttgcc agccatctgt tgtttgcccc tcccccgtgc cttccttgac    3000
cctggaaggt gccactccca ctgtcctttc ctaataaaat gaggaaattg catcgcattg    3060
tctgagtagg tgtcattcta ttctgggggg tggggtgggg caggacagca agggggagga    3120
ttgggaagac aatagcaggc atgctgggga tgcggtgggc tctatggctt ctgaggcgga    3180
aagaaccagc tggggctcta gggggtatcc ccacgcgccc tgtagcggcg cattaagcgc    3240
ggcgggtgtg gtggttacgc gcagcgtgac cgctacactt gccagcgccc tagcgcccgc    3300
tcctttcgct ttcttccctt cctttctcgc cacgttcgcc ggctttcccc gtcaagctct    3360
aaatcggggg ctccctttag ggttccgatt tagtgcttta cggcaccttc gaccccaaaa    3420
aacttgatta gggctgtgga atgtgtgtca gttagggtgt ggaaagtccc caggctcccc    3480
agcaggcaga agtatgcaaa gcatgcatct caattagtca gcaaccaggt gtggaaagtc    3540
cccaggctcc ccagcaggca gaagtatgca aagcatgcat ctcaattagt cagcaaccat    3600
agtcccgccc ctaactccgc ccatcccgcc cctaactccg cccagttccg cccattctcc    3660
gccccatggc tgactaattt ttttatttta tgcagaggcc gaggccgcct cggcctctga    3720
gctattccag aagtagtgag gaggcttttt tggaggccta ggcttttgca aaaagctctc    3780
tggctaacta gagaacccac tgcttactgg cttatcgaaa ttaatacgac tcactatagg    3840
gagacccaag ctggctagcg tttaaactta agcttggtac cgagctcgga tccactagtc    3900
cagtgtggtg gaattgccct ttccgcagag caatggcggt gtctgccggg tccgcgcgga    3960
cctcgcccag ctcagataaa gtacagaaag acaaggctga actgatctca gggcccaggc    4020
aggacagccg aatagggaaa ctcttggggtt ttgagtggac agatttgtcc agttggcgga    4080
```

-continued

```
ggctggtgac cctgctgaat cgaccaacgg accctgcaag cttagctgtc tttcgttttc    4140
tttttgggtt cttgatggtg ctagacattc cccaggagcg ggggctcagc tctctggacc    4200
ggaaatacct tgatgggctg gatgtgtgcc gcttcccctt gctggatgcc ctacgcccac    4260
tgccacttga ctggatgtat cttgtctaca ccatcatgtt tctgggggca ctgggcatga    4320
tgctgggcct gtgctaccgg ataagctgtg tgttattcct gctgccatac tggtatgtgt    4380
ttctcctgga caagacatca tggaacaacc actcctatct gtatgggttg ttggcctttc    4440
agctaacatt catggatgca aaccactact ggtctgtgga cggtctgctg aatgcccata    4500
ggaggaatgc ccacgtgccc ctttggaact atgcagtgct ccgtggccag atcttcattg    4560
tgtacttcat tgcgggtgtg aaaaagctgg atgcagactg ggttgaaggc tattccatgg    4620
aatatttgtc ccggcactgg ctcttcagtc ccttcaaact gctgttgtct gaggagctga    4680
ctagcctgct ggtcgtgcac tggggtgggc tgctgcttga cctctcagct ggtttcctgc    4740
tcttttttga tgtctcaaga tccattggcc tgttctttgt gtcctacttc cactgcatga    4800
attcccagct tttcagcatt ggtatgttct cctacgtcat gctggccagc agccctctct    4860
tctgctcccc tgagtggcct cggaagctgg tgtcctactg cccccgaagg ttgcaacaac    4920
tgttgcccct caaggcagcc cctcagccca gtgtttcctg tgtgtataag aggagccggg    4980
gcaaaagtgg ccagaagcca gggctgcgcc atcagctggg agctgccttc accctgctct    5040
acctcctgga gcagctattc ctgccctatt ctcattttct cacccagggc tataacaact    5100
ggacaaatgg gctgtatggc tattcctggg acatgatggt gcactcccgc tcccaccagc    5160
acgtgaagat cacctaccgt gatggccgca ctggcgaact gggctacctt aaccctgggg    5220
tatttacaca gagtcggcga tggaaggatc atgcagacat gctgaagcaa tatgccactt    5280
gcctgagccg cctgcttccc aagtataatg tcactgagcc ccagatctac tttgatattt    5340
gggtctccat caatgaccgc ttccagcaga ggattttga ccctcgtgtg gacatcgtgc    5400
aggccgcttg gtcaccccttt cagcgcacat cctgggtgca accactcttg atggacctgt    5460
ctccctggag ggccaagtta caggaaatca gagcagcct agacaaccac actgaggtgg    5520
tcttcattgc agatttccct ggactgcact tggagaattt tgtgagtgaa gacctgggca    5580
acactagcat ccagctgctg caggggggaag tgactgtgga gcttgtggca gaacagaaga    5640
accagactct tcgagaggga gaaaaaatgc agttgcctgc tggtgagtac cataaggtgt    5700
atacgacatc acctagccct tcttgctaca tgtacgtcta tgtcaacact acagagcttg    5760
cactggagca agacctggca tatctgcaag aattaaagga aaaggtggag aatgaagtg    5820
aaacagggcc tctacccccca gagctgcagc ctctgttgga aggggaagta aaaggggcc    5880
ctgagccaac acctctggtt cagacctttc ttagacgcca acaaaggctc caggagattg    5940
aacgccggcg aaatactcct ttccatgagc gattcttccg cttcttgttg cgaaagctct    6000
atgtctttcg ccgcagcttc ctgatgactt gtatctcact tcgaaatctg atattaggcc    6060
gtccttccct ggagcagctg gcccaggagg tgacttatgc aaacttgaga ccctttgagg    6120
cagttggaga actgaatccc tcaaacacgg attcttcaca ttctaatcct cctgagtcaa    6180
atcctgatcc tgtccactca gagttctgaa ggggccaga tgttggaagg gcaattcgag    6240
tctagagggc ccgccctgat agacggtttt tcgcccttttg acgttggagt ccacgttctt    6300
taatagtgga ctcttgttcc aaactggaac aacactcaac cctatctcgg tctattcttt    6360
tgatttataa gggattttgc cgatttcggc ctattggtta aaaaatgagc tgattaaca    6420
aaaatttaac gcgaattaat tctgtggaat gtgtgtcagt tagggtgtgg aaagtcccca    6480
```

-continued

| | | |
|---|---|---|
| ggctccccag caggcagaag tatgcaaagc atgcatctca attagtcagc aaccaggtgt | 6540 | |
| ggaaagtccc caggctcccc agcaggcaga agtatgcaaa gcatgcatct caattagtca | 6600 | |
| gcaaccatag tcccgcccct aactccgccc atcccgcccc taactccgcc cagttccgcc | 6660 | |
| cattctccgc cccatggctg actaattttt tttatttatg cagaggccga ggccgcctct | 6720 | |
| gcctctgagc tattccagaa gtagtgagga ggcttttttg gaggcctagg cttttgcaaa | 6780 | |
| aagctcccgg gagcttgtat atccattttc ggatctgatc aagagacagg atgaggatcg | 6840 | |
| tttcgcatga ttgaacaaga tggattgcac gcaggttctc cggccgcttg ggtggagagg | 6900 | |
| ctattcggct atgactgggc acaacagaca atcggctgct ctgatgccgc cgtgttccgg | 6960 | |
| ctgtcagcgc aggggcgccc ggttcttttt gtcaagaccg acctgtccgg tgccctgaat | 7020 | |
| gaactgcagg acgaggcagc gcggctatcg tggctggcca cgacgggcgt tccttgcgca | 7080 | |
| gctgtgctcg acgttgtcac tgaagcggga agggactggc tgctattggg cgaagtgccg | 7140 | |
| gggcaggatc tcctgtcatc tcaccttgct cctgccgaga aagtatccat catggctgat | 7200 | |
| gcaatgcggc ggctgcatac gcttgatccg gctacctgcc cattcgacca ccaagcgaaa | 7260 | |
| catcgcatcg agcgagcacg tactcggatg aagccggtc ttgtcgatca ggatgatctg | 7320 | |
| gacgaagagc atcaggggct cgcgccagcc gaactgttcg ccaggctcaa ggcgcgcatg | 7380 | |
| cccgacggcg aggatctcgt cgtgacccat ggcgatgcct gcttgccgaa tatcatggtg | 7440 | |
| gaaaatggcc gcttttctgg attcatcgac tgtggccggc tgggtgtggc ggaccgctat | 7500 | |
| caggacatag cgttggctac ccgtgatatt gctgaagagc ttggcggcga atgggctgac | 7560 | |
| cgcttcctcg tgctttacgg tatcgccgct cccgattcgc agcgcatcgc cttctatcgc | 7620 | |
| cttcttgacg agttcttctg agcgggactc tggggttcga atgaccgac caagcgacgc | 7680 | |
| ccaacctgcc atcacgagat ttcgattcca ccgccgcctt ctatgaaagg ttgggcttcg | 7740 | |
| gaatcgtttt ccgggacgcc ggctggatga tcctccagcg cggggatctc atgctggagt | 7800 | |
| tcttcgccca ccccaacttg tttattgcag cttataatgg ttacaaataa agcaatagca | 7860 | |
| tcacaaattt cacaaataaa gcatttttt cactgcattc tagttgtggt ttgtccaaac | 7920 | |
| tcatcaatgt atcttatcat gtctgtatac cgtcgacctc tagctagagc ttggcgtaat | 7980 | |
| catggtcata gctgtttcct gtgtgaaatt gttatccgct cacaattcca cacaacatac | 8040 | |
| gagccggaag cataaagtgt aaagcctggg gtgcctaatg agtgagctaa ctcacattaa | 8100 | |
| ttgcgttgcg ctcactgccc gctttccagt cgggaaacct gtcgtgccag ctgcattaat | 8160 | |
| gaatcggcca acgcgcgggg agaggcggtt tgcgtattgg gcgctcttcc gcttcctcgc | 8220 | |
| tcactgactc gctgcgctcg gtcgttcggc tgcggcgagc ggtatcagct cactcaaagg | 8280 | |
| cggtaatacg gttatccaca gaatcagggg ataacgcagg aaagaacatg tgagcaaaag | 8340 | |
| gccagcaaaa ggccaggaac cgtaaaaagg ccgcgttgct ggcgtttttc cataggctcc | 8400 | |
| gcccccctga cgagcatcac aaaaatcgac gctcaagtca gaggtggcga aacccgacag | 8460 | |
| gactataaag ataccaggcg tttccccctg gaagctccct cgtgcgctct cctgttccga | 8520 | |
| ccctgccgct taccggatac ctgtccgcct ttctcccttc gggaagcgtg gcgctttctc | 8580 | |
| atagctcacg ctgtaggtat ctcagttcgg tgtaggtcgt tcgctccaag ctgggctgtg | 8640 | |
| tgcacgaacc ccccgttcag cccgaccgct gcgccttatc cggtaactat cgtcttgagt | 8700 | |
| ccaacccggt aagacacgac ttatcgccac tggcagcagc cactggtaac aggattagca | 8760 | |
| gagcgaggta tgtaggcggt gctacagagt tcttgaagtg gtggcctaac tacggctaca | 8820 | |
| ctagaagaac agtatttggt atctgcgctc tgctgaagcc agttaccttc ggaaaaagag | 8880 | |

| | | |
|---|---|---|
| ttggtagctc ttgatccggc aaacaaacca ccgctggtag cggttttttt gtttgcaagc | 8940 | |
| agcagattac gcgcagaaaa aaaggatctc aagaagatcc tttgatcttt tctacggggt | 9000 | |
| ctgacgctca gtggaacgaa aactcacgtt aagggatttt ggtcatgaga ttatcaaaaa | 9060 | |
| ggatcttcac ctagatcctt ttaaattaaa aatgaagttt aaatcaatc taaagtatat | 9120 | |
| atgagtaaac ttggtctgac agttaccaat gcttaatcag tgaggcacct atctcagcga | 9180 | |
| tctgtctatt tcgttcatcc atagttgcct gactccccgt cgtgtagata actacgatac | 9240 | |
| gggagggctt accatctggc cccagtgctg caatgatacc gcgagaccca cgctcaccgg | 9300 | |
| ctccagattt atcagcaata aaccagccag ccggaagggc cgagcgcaga agtggtcctg | 9360 | |
| caactttatc cgcctccatc cagtctatta attgttgccg ggaagctaga gtaagtagtt | 9420 | |
| cgccagttaa tagtttgcgc aacgttgttg ccattgctac aggcatcgtg gtgtcacgct | 9480 | |
| cgtcgtttgg tatggcttca ttcagctccg gttcccaacg atcaaggcga gttacatgat | 9540 | |
| cccccatgtt gtgcaaaaaa gcggttagct ccttcggtcc tccgatcgtt gtcagaagta | 9600 | |
| agttggccgc agtgttatca ctcatggtta tggcagcact gcataattct cttactgtca | 9660 | |
| tgccatccgt aagatgcttt tctgtgactg gtgagtactc aaccaagtca ttctgagaat | 9720 | |
| agtgtatgcg gcgaccgagt tgctcttgcc cggcgtcaat acgggataat accgcgccac | 9780 | |
| atagcagaac tttaaaagtg ctcatcattg gaaaacgttc ttcggggcga aaactctcaa | 9840 | |
| ggatcttacc gctgttgaga tccagttcga tgtaacccac tcgtgcaccc aactgatctt | 9900 | |
| cagcatcttt tactttcacc agcgtttctg ggtgagcaaa aacaggaagg caaaatgccg | 9960 | |
| caaaaaaggg aataagggcg acacggaaat gttgaatact catactcttc ctttttcaat | 10020 | |
| attattgaag catttatcag ggttattgtc tcatgagcgg atacatattt gaatgtattt | 10080 | |
| agaaaaataa acaaataggg gttccgcgca catttccccg aaaagtgcca cctgacgtc | 10139 | |

<210> SEQ ID NO 22
<211> LENGTH: 6115
<212> TYPE: DNA
<213> ORGANISM: Artificial Sequence
<220> FEATURE:
<223> OTHER INFORMATION: Synthetic construct-VKORhygro

<400> SEQUENCE: 22

| | | |
|---|---|---|
| gacggatcgg gagatctccc gatccctat ggtcgactct cagtacaatc tgctctgatg | 60 | |
| ccgcatagtt aagccagtat ctgctccctg cttgtgtgtt ggaggtcgct gagtagtgcg | 120 | |
| cgagcaaaat ttaagctaca acaaggcaag cttgaccga caattgcatg aagaatctgc | 180 | |
| ttagggttag gcgttttgcg ctgcttcgcg atgtacgggc cagatatacg cgttgacatt | 240 | |
| gattattgac tagttattaa tagtaatcaa ttacggggtc attagttcat agcccatata | 300 | |
| tggagttccg cgttacataa cttacggtaa atggcccgcc tggctgaccg cccaacgacc | 360 | |
| cccgcccatt gacgtcaata atgacgtatg ttcccatagt aacgccaata gggactttcc | 420 | |
| attgacgtca atgggtggac tatttacggt aaactgccca cttggcagta catcaagtgt | 480 | |
| atcatatgcc aagtacgccc cctattgacg tcaatgacgg taaatggccc gcctggcatt | 540 | |
| atgcccagta catgacctta tgggactttc ctacttggca gtacatctac gtattagtca | 600 | |
| tcgctattac catggtgatg cggttttggc agtacatcaa tgggcgtgga tagcggtttg | 660 | |
| actcacgggg atttccaagt ctccacccca ttgacgtcaa tgggagtttg ttttggcacc | 720 | |
| aaaatcaacg ggactttcca aaatgtcgta acaactccgc cccattgacg caaatgggcg | 780 | |
| gtaggcgtgt acggtgggag gtctatataa gcagagctct ctggctaact agagaaccca | 840 | |

```
ctgcttactg gcttatcgaa attaatacga ctcactatag ggagacccaa gctggctagc    900
gtttaaactt aagcttggta ccgagctcgg atccactagt ccagtgtggt ggaattgccc    960
ttcaccatgg gcagcacctg ggggagccct ggctgggtgc ggctcgctct ttgcctgacg   1020
ggcttagtgc tctcgctcta cgcgctgcac gtgaaggcgg cgcgcgcccg ggaccgggat   1080
taccgcgcgc tctgcgacgt gggcaccgcc atcagctgtt cgcgcgtctt ctcctccagg   1140
tggggcaggg gtttcgggct ggtggagcat gtgctgggac aggacagcat cctcaatcaa   1200
tccaacagca tattcggttg catcttctac acactacagc tattgttagg ttgcctgcgg   1260
acacgctggg cctctgtcct gatgctgctg agctccctgg tgtctctcgc tggttctgtc   1320
tacctggcct ggatcctgtt cttcgtgctc tatgatttct gcattgtttg tatcaccacc   1380
tatgctatca acgtgagcct gatgtggctc agtttccgga aggtccaaga accccagggc   1440
aaggctaaga ggcactgaac aagggcaatt ctgcagatat ccagcacagt ggcggccgct   1500
cgagtctaga gggcccgttt aaacccgctg atcagcctcg actgtgcctt ctagttgcca   1560
gccatctgtt gtttgcccct cccccgtgcc ttccttgacc ctggaaggtg ccactcccac   1620
tgtcctttcc taataaaatg aggaaattgc atcgcattgt ctgagtaggt gtcattctat   1680
tctggggggt ggggtggggc aggacagcaa gggggaggat tgggaagaca atagcaggca   1740
tgctggggat gcggtgggct ctatggcttc tgaggcggaa agaaccagct ggggctctag   1800
ggggtatccc cacgcgccct gtagcggcgc attaagcgcg gcgggtgtgg tggttacgcg   1860
cagcgtgacc gctacacttg ccagcgccct agcgcccgct cctttcgctt tcttcccttc   1920
ctttctcgcc acgttcgccg gctttccccg tcaagctcta aatcggggca tccctttagg   1980
gttccgattt agtgctttac ggcacctcga ccccaaaaaa cttgattagg gtgatggttc   2040
acgtagtggg ccatcgccct gatagacggt ttttcgccct ttgacgttgg agtccacgtt   2100
ctttaatagt ggactcttgt tccaaactgg aacaacactc aaccctatct cggtctattc   2160
ttttgattta agggatttt g gggatttc g gcctattgg ttaaaaaatg agctgattta   2220
acaaaaattt aacgcgaatt aattctgtgg aatgtgtgtc agttagggtg tggaaagtcc   2280
ccaggctccc caggcaggca gaagtatgca aagcatgcat ctcaattagt cagcaaccag   2340
gtgtggaaag tccccaggct ccccagcagg cagaagtatg caaagcatgc atctcaatta   2400
gtcagcaacc atagtcccgc ccctaactcc gcccatcccg cccctaactc cgcccagttc   2460
cgcccattct ccgccccatg ctgactaatt ttttttattt atgcagaggc cgaggccgc    2520
ctctgcctct gagctattcc agaagtagtg aggaggcttt tttggaggcc taggcttttg   2580
caaaaagctc ccgggagctt gtatatccat tttcggatct gatcagcacg tgatgaaaaa   2640
gcctgaactc accgcgacgt ctgtcgagaa gtttctgatc gaaaagttcg acagcgtctc   2700
cgacctgatg cagctctcgg agggcgaaga atctcgtgct ttcagcttcg atgtaggagg   2760
gcgtggatat gtcctgcggg taaatagctg cgccgatggt ttctacaaag atcgttatgt   2820
ttatcggcac tttgcatcgg ccgcgctccc gattccggaa gtgcttgaca ttgggggaatt   2880
cagcgagagc ctgacctatt gcatctcccg ccgtgcacag ggtgtcacgt tgcaagacct   2940
gcctgaaacc gaactgcccg ctgttctgca gccggtcgcg gaggccatgg atgcgatcgc   3000
tgcggccgat cttagccaga cgagcgggtt cggcccattc ggaccgcaag gaatcggtca   3060
atacactaca tggcgtgatt tcatatgcgc gattgctgat ccccatgtgt atcactggca   3120
aactgtgatg gacgacaccg tcagtgcgtc cgtcgcgcag gctctcgatg agctgatgct   3180
ttgggccgag gactgccccg aagtccggca cctcgtgcac gcggatttcg ctccaacaa    3240
```

```
tgtcctgacg gacaatggcc gcataacagc ggtcattgac tggagcgagg cgatgttcgg    3300
ggattcccaa tacgaggtcg ccaacatctt cttctggagg ccgtggttgg cttgtatgga    3360
gcagcagacg cgctacttcg agcggaggca tccggagctt gcaggatcgc cgcggctccg    3420
ggcgtatatg ctccgcattg gtcttgacca actctatcag agcttggttg acggcaattt    3480
cgatgatgca gcttgggcgc agggtcgatg cgacgcaatc gtccgatccg agccgggac    3540
tgtcgggcgt acacaaatcg cccgcagaag cgcggccgtc tggaccgatg gctgtgtaga    3600
agtactcgcc gatagtggaa accgacgccc cagcactcgt ccgagggcaa aggaatagca    3660
cgtgctacga gatttcgatt ccaccgccgc cttctatgaa aggttgggct tcggaatcgt    3720
tttccgggac gccggctgga tgatcctcca gcgcgggat ctcatgctgg agttcttcgc    3780
ccaccccaac ttgtttattg cagcttataa tggttacaaa taaagcaata gcatcacaaa    3840
tttcacaaat aaagcatttt tttcactgca ttctagttgt ggtttgtcca aactcatcaa    3900
tgtatcttat catgtctgta taccgtcgac ctctagctag agcttggcgt aatcatggtc    3960
atagctgttt cctgtgtgaa attgttatcc gctcacaatt ccacacaaca tacgagccgg    4020
aagcataaag tgtaaagcct ggggtgccta atgagtgagc taactcacat taattgcgtt    4080
gcgctcactg cccgctttcc agtcgggaaa cctgtcgtgc cagctgcatt aatgaatcgg    4140
ccaacgcgcg gggagaggcg gtttgcgtat tgggcgctct tccgcttcct cgctcactga    4200
ctcgctgcgc tcggtcgttc ggctgcggcg agcggtatca gctcactcaa aggcggtaat    4260
acggttatcc acagaatcag gggataacgc aggaaagaac atgtgagcaa aaggccagca    4320
aaaggccagg aaccgtaaaa aggccgcgtt gctggcgttt ttccataggc tccgcccccc    4380
tgacgagcat cacaaaaatc gacgctcaag tcagaggtgg cgaaacccga caggactata    4440
aagataccag gcgtttcccc ctggaagctc cctcgtgcgc tctcctgttc cgaccctgcc    4500
gcttaccgga tacctgtccg cctttctccc ttcgggaagc gtggcgcttt ctcaatgctc    4560
acgctgtagg tatctcagtt cggtgtaggt cgttcgctcc aagctgggct gtgtgcacga    4620
accccccgtt cagcccgacc gctgcgcctt atccggtaac tatcgtcttg agtccaaccc    4680
ggtaagacac gacttatcgc cactggcagc agccactggt aacaggatta gcagagcgag    4740
gtatgtaggc ggtgctacag agttcttgaa gtggtggcct aactacggct acactagaag    4800
gacagtattt ggtatctgcg ctctgctgaa gccagttacc ttcggaaaaa gagttggtag    4860
ctcttgatcc ggcaaacaaa ccaccgctgg tagcggtggt ttttttgttt gcaagcagca    4920
gattacgcgc agaaaaaaag gatctcaaga agatcctttg atcttttcta cggggtctga    4980
cgctcagtgg aacgaaaact cacgttaagg gattttggtc atgagattat caaaaaggat    5040
cttcacctag atccttttaa attaaaaatg aagttttaaa tcaatctaaa gtatatatga    5100
gtaaacttgg tctgacagtt accaatgctt aatcagtgag gcacctatct cagcgatctg    5160
tctatttcgt tcatccatag ttgcctgact ccccgtcgtg tagataacta cgatacggga    5220
gggcttacca tctggcccca gtgctgcaat gataccgcga cccacgct caccggctcc    5280
agatttatca gcaataaacc agccagccgg aagggccgag cgcagaagtg gtcctgcaac    5340
tttatccgcc tccatccagt ctattaattg ttgccgggaa gctagagtaa gtagttcgcc    5400
agttaatagt ttgcgcaacg ttgttgccat tgctacaggc atcgtggtgt cacgctcgtc    5460
gtttggtatg gcttcattca gctccggttc ccaacgatca aggcgagtta catgatcccc    5520
catgttgtgc aaaaaagcgg ttagctcctt cggtcctccg atcgttgtca gaagtaagtt    5580
ggccgcagtg ttatcactca tggttatggc agcactgcat aattctctta ctgtcatgcc    5640
```

-continued

```
atccgtaaga tgcttttctg tgactggtga gtactcaacc aagtcattct gagaatagtg    5700
tatgcggcga ccgagttgct cttgcccggc gtcaatacgg gataataccg cgccacatag    5760
cagaacttta aaagtgctca tcattggaaa acgttcttcg gggcgaaaac tctcaaggat    5820
cttaccgctg ttgagatcca gttcgatgta acccactcgt gcacccaact gatcttcagc    5880
atcttttact ttcaccagcg tttctgggtg agcaaaaaca ggaaggcaaa atgccgcaaa    5940
aaagggaata agggcgacac ggaaatgttg aatactcata ctcttccttt ttcaatatta    6000
ttgaagcatt tatcagggtt attgtctcat gagcggatac atatttgaat gtatttagaa    6060
aaataaacaa atagggttc cgcgcacatt tccccgaaaa gtgccacctg acgtc          6115
```

COMPOSITIONS AND METHODS FOR PRODUCING GAMMA-CARBOXYLATED PROTEINS

CROSS REFERENCE TO RELATED APPLICATIONS

This application is a national phase application under 35 U.S.C. §371 of PCT International Application No. PCT/SE2006/000426, filed Apr. 10, 2006, which claims priority to Swedish Application Serial No. 0500831-3, filed Apr. 13, 2005.

TECHNICAL FIELD

The present invention relates a host cell comprising an expression vector comprising a nucleic acid molecule encoding a protein requiring gamma-carboxylation and associated expression control sequences and a nucleic acid molecule encoding a vitamin K epoxido reductase and associated expression control sequences, and a γ-glutamyl carboxylase and associated control sequences. The invention further relates to a method of producing a protein requiring gamma-carboxylation in high yields.

BACKGROUND TO THE INVENTION

Bleeding is a common clinical problem. It is a consequence of disease, trauma, surgery and medicinal treatment. It is imperative to mechanically stop the bleeding. This may be difficult or even impossible due to the location of the bleeding or because it diffuses from many (small) vessels. Patients who are bleeding may thus require treatment with agents that support haemostasis. This may be blood-derived products (haemotherapy), agents that cause the release of endogenous haemostatic agents, recombinant coagulation factors (F), or agents that delay the dissolution of blood clots.

The first line treatment among the blood derived products, often obtained from the local hospital, are whole blood for volume substitution and support of haemostasis, packed red cells for the improvement of oxygen transporting capacity, platelet concentrates to raise the number of platelets (if low or defective) and fresh frozen plasma for support of the haemostasis (blood coagulation and platelet aggregation). Second line plasma derived products that support haemostasis are plasma cryoprecipitate, prothrombin complex concentrates, activated prothrombin complex concentrates and purified coagulation factors. Several coagulation factors are today available as human recombinant proteins, inactive (coagulation factors VIII and IX) and activated (coagulation factor VIIa).

Haemophilia is an inherited or acquired bleeding disorder with either abnormal or deficient coagulation factor or antibodies directed towards a coagulation factor which inhibits the procoagulant function. The most common haemophilias are haemophilia A (lack coagulation factor VIII) and haemophilia B (factor IX). The purified or recombinant single coagulation factors are the main treatment of patients with haemophilia. Patients with inhibitory antibodies posses a treatment problem as they may also neutralise the coagulation factor that is administered to the patient.

The active form of Protein C (APC) is an inhibitor of plasma coagulation by degradation of the activated coagulation factors Va and VIIIa. Recombinant APC has been shown to be an effective treatment of undue plasma coagulation in patients with sepsis.

Coagulation factors for therapeutic use can be obtained from human plasma, although the purification process is not simple and requires many steps of which several aim at eliminating contaminating viruses. But even with extensive safety measures and testing of blood-derived products, contamination with infectious viruses or prions cannot be ruled out. Because of this risk it is highly desirable to produce human therapeutic proteins from recombinant cells grown in media without animal derived components. This is not always straightforward as many proteins require a mammalian host to be produced in a fully functional form, i.e. be correctly post-translationally modified. Among the coagulation factors commercially produced in recombinant cells are FVII (NovoSeven), FVIII (Kogenate, Recombinate, Refacto) and FIX (BeneFix) (Roddie and Ludlam. Blood Rev. 11:169-177, 1997) and Active Protein C (Xigris). One of the major obstacles in obtaining large amounts of fully functional recombinant human coagulation factors lies in the Gla-domain present in FII, FVII, FIX, FX, Protein S and Protein C. This domain contains glutamic acid residues that are post-translationally modified by addition of carboxyl groups. The production of these factors are hampered by the fact that over-expression of them result in under-carboxylated, and hence inactive, protein. The Gla modifications are a result of the action of a vitamin K-dependent enzyme called γ-glutamyl carboxylase (GGCX). This enzyme has been extensively studied by many scientists, particularly those involved in coagulation factor research (WO-A-8803926; Wu et al. Science 254(5038):1634-1636, 1991; Rehemtulla et al, Proc Natl Acad Sci USA 90:4611-4615, 1993; Stanley J. Biol. Chem. 274(24):16940-16944, 1999; Vo et al., FEBS letters 445:256-260, 1999; Begley et al, The Journal of Biological Chemistry 275(46):36245-36249, 2000; Walker et al., The Journal of Biological Chemistry 276(11):7769-7774, 2001; Bandyopadhyay, et al. Proc Natl Acad Sci USA 99(3):1264-1269, 2002; Czerwiec et al., Eur J Biochem 269:6162-6172, 2002; Hallgren et al, Biochemistry 41(50):15045-15055, 2002; Harvey et al., The Journal of Biological Chemistry 278(10):8363-8369, 2003). Attempts to co-express GGCX with coagulation factor FIX has been tried by at least two scientific groups but were not successful (Rehemtulla, et al. 1993, ibid; Hallgren et al. 2002, ibid). Considering the large interest in GGCX enzymes, it may be assumed that many more trials have failed and thus have not been reported. GGCX requires reduced vitamin K as a cofactor. The reduced vitamin K is by GGCX converted to vitamin K epoxide, which is recycled to reduced vitamin K by Vitamin K epoxidoreductase (VKOR). Thus for efficient vitamin K dependent carboxylation of proteins two enzymes are required, GGCX and VKOR. Cloning and identification of VKOR was reported 2004 (Li et al, Nature 427:541-543, 2004, Rost et al., Nature 427:537-541, 2004). The VKOR protein is a 163 amino acid polypeptide with at least one predicted transmembrane region. From recombinant cells expressing VKOR activity is localized to the microsomal subcellular fraction.

For human FII (prothrombin) at least 8 out of 10 Glu residues have to be correctly modified in order to obtain fully functional prothrombin (Malhotra, et al., J. Biol. Chem. 260: 279-287, 1985; Seegers and Walz Prothrombin and other vitamin K proteins', CRC Press, 1986). Similarity, human coagulation factor IX clotting activity require γ-carboxylation of at lest 10 out of 12 glutamic residues in the Gla-domain (White et al, Thromb. Haemost. 78:261-265, 1997). Extensive efforts to obtain high production levels of rhFII have been made using several different systems such as CHO cells, BHK cells, 293cells and vaccinia virus expression systems, but have all failed or resulted in an under-carboxylated product and thus functionally inactive prothrombin (Jørgensen et al., J. Biol. Chem. 262:6729-6734, 1987; Russo et al., Biotechnol Appl Biochem 14(2):222-233, 1991; Fischer et al, J Biotechnol 38(2):129-136, 1995; Herlitschka et al. Protein Expr. Purif. 8(3):358-364, 1996; Russo et al, Protein Expr. Purif. 10:214-225, 1997; Vo et al. 1999, ibid; Wu and Suttie Thromb Res 96(2):91-98, 1999). Earlier reported productivities for carboxylated recombinant human prothrombin are low; 20 mg/L for mutant prothrombin (Côte et al., J. Biol. Chem 269:11374-11380, 1994), 0.55 mg/L for human prothrombin expressed in CHO cells (fully carboxylated, Jøergensen et al. 1987, ibid), 25 mg/L in CHO cells (degree of carboxylation not shown, Russo et al. 1997, ibid).

As far as known co-expression of a protein requiring γ-carboxylation and VKOR has not been reported earlier.

WO 92/19636 discloses the cloning and sequence identification of a human and bovine vitamin K dependent carboxylase. The application suggests co-expressing the vitamin K dependent carboxylase and a vitamin K dependent protein in a suitable host cell in order to prepare the vitamin K dependent protein. No co-expression of the carboxylase and vitamin K dependent protein is exemplified.

WO 92/19636 discloses the cloning and sequence identification of a human and bovine vitamin K dependent carboxylase. The application suggests co-expressing the vitamin K dependent carboxylase (GGCX) and a vitamin K dependent protein in a suitable host cell in order to prepare the vitamin K dependent protein. No co-expression of the carboxylase and vitamin K dependent protein is exemplified.

WO 2005/038019 claims a method of increasing the overall productivity of γ-carboxylated protein by a controlled co-expression of γ-carboxylated protein and GGCX. The invention is exemplified with improved productivity of coagulation factors II and FIX.

WO 2005/030039 suggests co-expression of vitamin K dependent proteins with Vitamin K epoxide reductase (VKOR) in order to improve γ-carboxylation. However, no such co-expression expression is exemplified.

Co-expression of coagulation factor X (FX) and VKOR has been shown to improve the share of γ-carboxylated protein by Sun et al. (Blood 106: 3811-3815, 2005). Wajih et al. (JBC 280:31603-31607, 2005) has in addition demonstrated improved share of γ-carboxylated coagulation factor IX (FIX) by co-expression with VKOR. Both publications reported that VKOR incresed the share of γ-carboxylated protein but VKOR co-expression did not improve the overall productivity of coagulation factor.

There is a need for improved methods to produce activated blood clotting factors in high yields. The present invention sets out to address this need.

SUMMARY OF THE INVENTION

According to a first aspect of the invention there is provided a host cell comprising an expression vector comprising a nucleic acid molecule encoding a protein requiring gamma-carboxylation and associated expression control sequences, and an expression vector comprising a nucleic acid molecule encoding a vitamin K epoxidoreductase and associated expression control sequences, wherein the host cell further comprises a nucleic acid molecule encoding a γ-glutamyl carboxylase and associated expression control sequences.

In another aspect, a cell is provided which is engineered to express (i) a protein which requires gamma-carboxylation, and (ii) vitamin K epoxidoreductase, wherein the proteins (i) and (ii) are expressed in a ratio between 10:1 and 500:1.

According to a further aspect a genetically modified eukaryotic host cell is provided comprising: (i) a polynucleotide encoding vitamin K epoxidoreductase protein wherein said vitamin K epoxidoreductase protein encoding sequence is operably linked to expression control sequences permitting expression of vitamin K epoxidoreductase protein by said cell; (ii) a polynucleotide encoding a protein requiring carboxylation by the γ-glutamyl carboxylase protein operably linked to expression control sequences permitting expression of said protein requiring carboxylation by said cell, and (iii) a polynucleotide encoding gamma-glutamyl carboxylase According to yet another aspect a vector is provided comprising a nucleic acid molecule encoding a protein requiring gamma-carboxylation and associated expression control sequences and a nucleic acid molecule encoding a vitamin K epoxidoreductase and associated expression control sequences.

According to another aspect a method is provided for producing gamma-carboxylated protein comprising:(i) culturing a cell expressing a recombinant protein which requires gamma-carboxylation, vitamin K epoxidoreductase and a γ-glutamyl carboxylase and (ii) isolating gamma-carboxylated protein.

According to another aspect a method is provided of producing a pharmaceutical composition suitable for inducing blood clotting or promoting increased or decreased coagulation, comprising purifying active carboxylated protein produced according to the above methods and admixing the purified carboxylated protein with one or more pharmaceutically acceptable carriers or excipients.

According to a further aspect a method is provided of promoting increased or decreased coagulation in a subject comprising administering a pharmacologically effective amount of an isolated gamma-carboxylated protein obtained by the above methods to a patient in need thereof.

The protein requiring gamma-carboxylation produced by the methods of the present invention can be used in haemostatic or antithrombothic therapy.

DETAILED DESCRIPTION OF THE INVENTION

Figure 1:
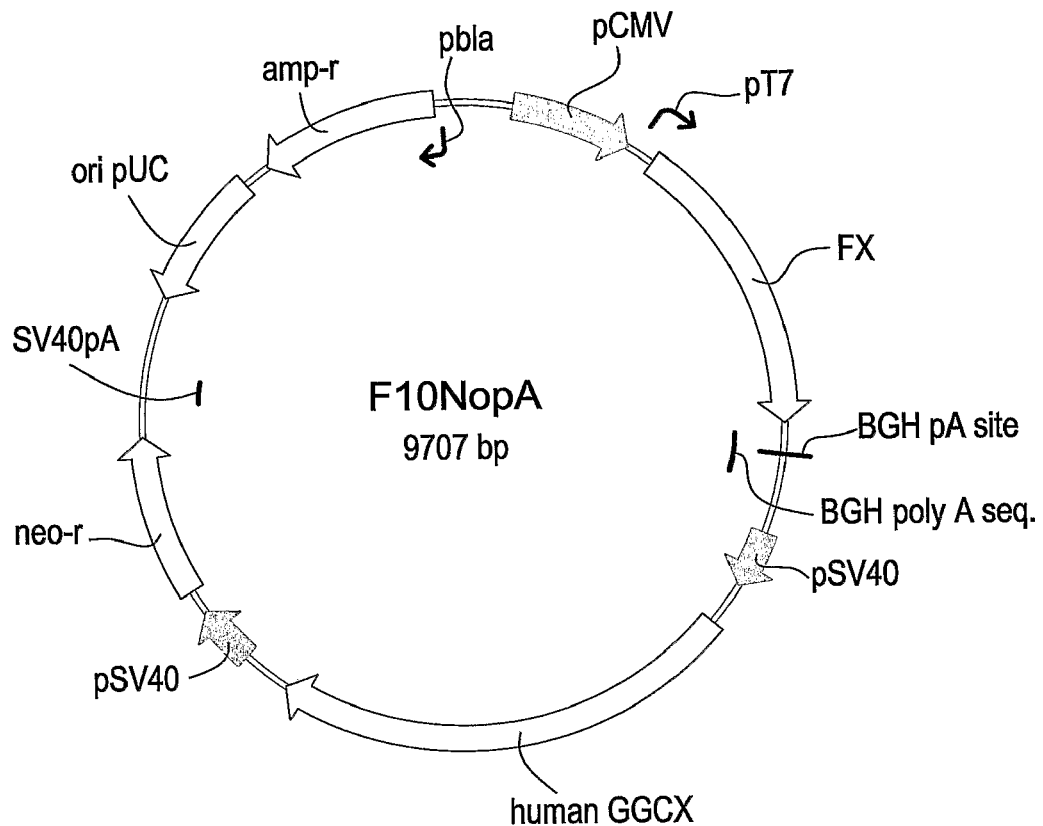
FIG. 1 shows a plasmid map of F10NopA (factor X+GGCX) co-expression vector and a plasmid map of VKORzeo (VKOR) expression vector.
Figure 1:
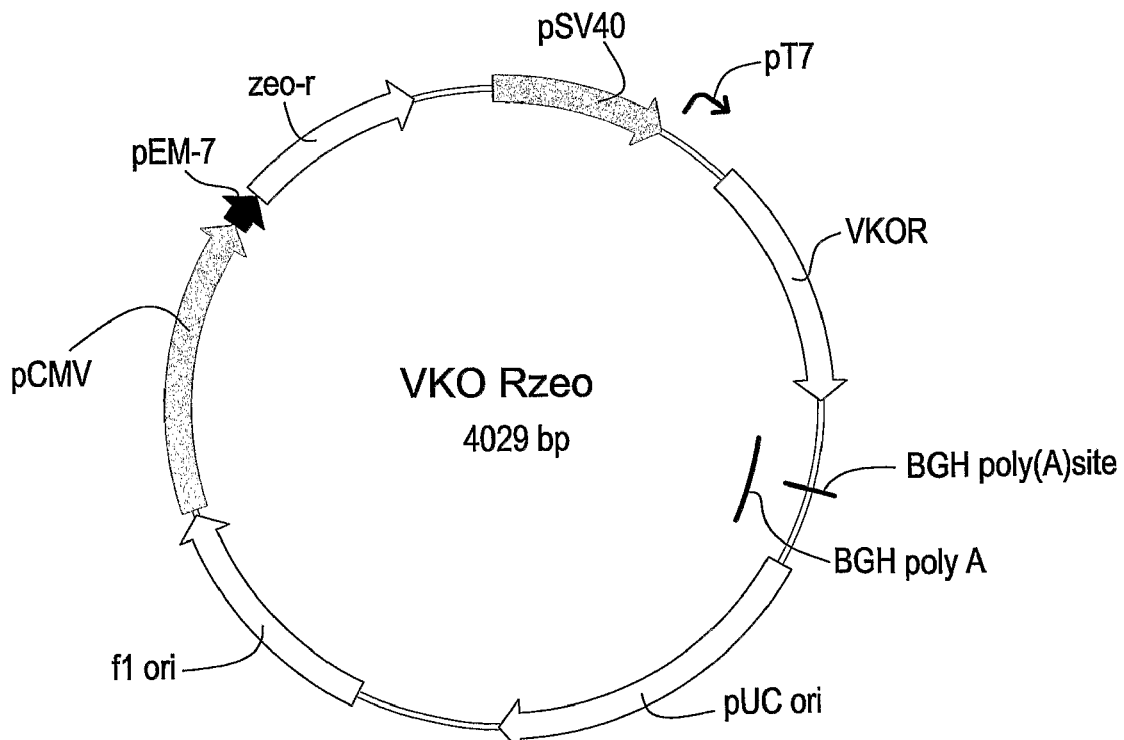

According to a first aspect of the invention there is provided a host cell comprising an expression vector comprising a nucleic acid molecule encoding a protein requiring gamma-carboxylation and associated expression control sequences, and an expression vector comprising a nucleic acid molecule encoding a vitamin K epoxidoreductase and associated expression control sequences, wherein the host cell further comprises a nucleic acid molecule encoding a γ-glutamyl carboxylase and associated expression control sequences.

In one embodiment said nucleic acid molecule encoding a protein requiring gamma-carboxylation and associated expression control sequences comprises a first promoter, and said nucleic acid molecule encoding a vitamin K epoxidoreductase and associated expression control sequences comprises a second promoter. In another embodiment the first promoter is sufficiently stronger than the second promoter so that the protein requiring gamma-carboxylation and the vitamin K epoxidoreductase are expressed in a ratio of at least 10:1. In another embodiment the first promoter is sufficiently stronger than the second promoter so that the protein requiring gamma-carboxylation and the vitamin K epoxidoreductase are expressed in a ratio of at least 5:1.

In another embodiment the cell further comprises a nucleic acid molecule encoding a γ-glutamyl carboxylase and associated expression control sequences. In one embodiment, the nucleic acid molecule encoding a γ-glutamyl carboxylase and associated expression control sequences further comprises a third promoter, wherein the first promoter is sufficiently stronger than the third promoter so that the protein requiring gamma-carboxylation and the γ-glutamyl carboxylase are expressed in a ratio of at least 10:1. In another embodiment the first promoter is sufficiently stronger than the second promoter so that the protein requiring gamma-carboxylation and the vitamin K epoxidoreductase are expressed in a ratio of at least 5:1.

The first promoter can be human cytomegalovirus (hCMV) immediate-early promoter and the second and third promoter can be SV40 early promoter.

In one particular embodiment, both the nucleic acid molecule encoding the protein requiring gamma-carboxylation and associated expression control sequences, and the nucleic acid molecule encoding the Vitamin K epoxidoreductase, and optionally the γ-glutamyl carboxylase, and associated expression control sequences are located on the same expression vector. In another embodiment these two or optionally three nucleic acid molecules are located on two or more separate expression vectors.

In another aspect a cell is provided which is engineered to express (i) a protein which requires gamma-carboxylation, and (ii) vitamin K epoxidoreductase, wherein the proteins (i) and (ii) are expressed in a ratio between 10:1 and 500:1. In another embodiment, the proteins (i) and (ii) are expressed in a ratio between 5:1 and 500:1

The protein which requires gamma-carboxylation is selected from the group consisting of: coagulation factor VII, coagulation FVII, coagulation factor IX, coagulation FIX, prothrombin, coagulation factor II, coagulation FII, coagulation factor X, coagulation FX, and their activated forms FVIIa, FIXa, FXa, Protein C, Protein S, Protein Z, Bone Gla protein, Matrix Gla protein, Growth arrest-specific protein 6, snake venom proteases similar to coagulation factors such as Factor X-like snake venom proteases, and Acanthophiinae FXa-like protein.

In one embodiment, the protein which requires gamma-carboxylation is a vitamin K dependent coagulation factor. In another embodiment, the protein which requires gamma-carboxylation is Factor FX. In a third embodiment, the protein which requires gamma-carboxylation is prothrombin. In a forth embodiment, the protein which requires gamma-carboxylation is Factor X. In a fifth embodiment, the protein which requires gamma-carboxylation is factor VII.

The protein which requires gamma-carboxylation is preferably a human protein but all eukaryotic proteins is encompassed by the invention. Vitamin K epoxidoreductase is preferably a human protein but all eukaryotic Vitamin K epoxidoreductases can be used in the present invention, γ-glutamyl carboxylase is preferably a human protein but all eukaryotic γ-glutamyl carboxylases can be used in the present invention.

According to a further aspect a genetically modified eukaryotic host cell is provided comprising:
(i) a polynucleotide encoding vitamin K epoxidoreductase protein wherein said vitamin K epoxidoreductase protein encoding sequence is operably linked to expression control sequences permitting expression of vitamin K epoxidoreductase protein by said cell; and
(ii) a polynucleotide encoding a protein requiring carboxylation by the γ-glutamyl carboxylase protein operably linked to expression control sequences permitting expression of said protein requiring carboxylation by said cell.
(iii) a polynucleotide encoding gamma-glutamyl carboxylase wherein said gamma-glutamyl carboxylase protein encoding sequence is operably linked to expression control sequences permitting expression of gamma-glutamyl carboxylase protein by said cell In one embodiment, the cell is capable of expressing the vitamin K epoxidoreductase protein and the protein requiring carboxylation in the ratio of at least 1:10. In another embodiment, said ratio is at least 1:5.

The host cell is preferably a eukaryotic cell. Typical host cells include, but are not limited to insect cells, yeast cells, and mammalian cells. Mammalian cells are particularly preferred. Suitable mammalian cells lines include, but are not limited to, CHO, HEK, NS0, 293, Per C.6, BHK and COS cells, and derivatives thereof. In one embodiment the host cell is the mammalian cell line CHO-S.

According to yet another aspect a vector is provided comprising a nucleic acid molecule encoding a protein requiring gamma-carboxylation and associated expression control sequences and a nucleic acid molecule encoding a vitamin K epoxidoreductase and associated expression control sequences. In one embodiment the nucleic acid molecule encodes a protein requiring gamma-carboxylation and associated expression control sequences comprises a first promoter, and the nucleic acid molecule encoding a vitamin K epoxidoreductase and associated expression control sequences comprises a second promoter. The first promoter can be sufficiently stronger than the second promoter so that the protein requiring gamma-carboxylation and the vitamin K epoxidoreductase are expressed in a ratio of at least 10:1. In another embodiment this ratio is 5:1. The vector could also comprise a nucleic acid molecule encoding a γ-glutamyl carboxylase and associated expression control sequences. Said nucleic acid molecule encoding a γ-glutamyl carboxylase and associated expression control sequences could comprise a third promoter, wherein the first promoter is sufficiently stronger than the third promoter so that the protein requiring gamma-carboxylation and γ-glutamyl carboxylase are expressed in a ratio of at least 10:1. In another embodiment this ratio is 5:1. The protein which requires gamma-carboxylation can be selected from the group consisting of: coagulation factor VII, coagulation FVII, coagulation factor IX, coagulation FIX, prothrombin, coagulation factor II, coagulation FII, coagulation factor X, coagulation FX, and their activated forms FVIIa, FIXa, Fxa, snake venom proteases similar to coagulation factors such as Factor X-like snake venom proteases and Acanthophiinae FXa-like protein, Protein C, Protein S, Protein Z, Bone Gla protein, Matrix Gla protein, Growth arrest-specific protein 6.

According to another aspect a method is provided for producing gamma-carboxylated protein comprising: (i) culturing a cell expressing a recombinant protein which requires gamma-carboxylation, vitamin K epoxidoreductase and a γ-glutamyl carboxylase and (ii) isolating gamma-carboxylated protein.

Said cell expresses the protein which requires gamma-carboxylation and vitamin K epoxidoreductase in a ratio of at least 10:1, under conditions suitable for expression of both proteins.

The vitamin K dependent coagulation factors (FII, FVII, FIX, FX and their activated forms FIIa or thrombin, FVIIa, FIXa, FXa) produced by the present method of co-expression with VKOR alone or in combination with GGCX can be expected to be useful in the prevention and treatment of bleeding following trauma, surgery or diseases of the liver, kidneys, platelets or blood coagulation factors (haemophilia). Likewise the coagulation factor Protein C and its activated form APC can be expected to be useful in the prevention and suitable proteins are: FXa-like protein in venom of elapid snake (subfamily Acanthophiinae) and cone snail venom (*Conus textile*).

Each of these proteins, including their nucleic acid and amino acid sequences, are well known. Table 1 identifies representative sequences of wild-type and mutant forms of the various proteins that can be used in the present invention.

TABLE 1

| DESCRIPTION | CDNA EMBL ACC# | SPLICE VARIANTS (PROTEIN) | MUTATIONS | GENE EMBL ACC# |
|---|---|---|---|---|
| Glutamate gamma carboxylase | BC013979 | 2; BC013979; AF253530 | 1 SNP (EMBL# U65896); 2 SNPs (OMIM# 137167) | U65896 |
| Prothrombin | V00595 | 1; V00595 | approx. 100 SNP's (EMBL# AF478696) | AF478696 |
| Factor VII | AF466933 | 4; AF466933; AF272774; AR030786; AAN60063 | 21 SNPs (OMIM# 277500) | J02933 |
| Factor IX | A01819 | 3; A01819; A34669; M19063 | 5 SNPs (EMBL# AF536327); 108 SNPs (OMIM# 306900) | AF536327 |
| Factor X | BC046125 | 4; BC040125; M57285; AR095306; AB005892 | 118 SNPs (EMBL# AF503510); 14 SNPs (OMIM# 227600) | AF503510 |
| Protein C | BC034377 | 7; AB083690; AB083693; I09623; S50739; S72338 | 57 SNPs (EMBL# AF378903); 25 SNPs (OMIM# 176860) | AF378903 |
| Osteocalcin | AF141310 | 5; AF141310; AF141310; BC033656; X04143; X51699 | | X04143 |
| Matrix GLA protein | BC005272 | 1; BC005272 | | |
| Growth arrest-specific 6; AXL stimulatory factor | BC038984 | 1; BC038984 | | |
| Protein Z | M55670 | 2; AB033749; AB033749 | | |
| Proline-rich Gla (G-carboxyglutamic acid) polypeptide 1 | AF009242 | 2; AF009242; BC030786 | | |
| Proline-rich Gla (G-carboxyglutamic acid) polypeptide 2 | AF009243 | 2; AF009243; BC026032 | | |
| Vitamin K-dependent protein S precursor | BC015801 | 1; BC015801 | approx. 100 SNPs (EMBL# AY308744); 8 SNPs (OMIM# 176880) | AY308744 |
| Snake venom FX-like proteases | AY769963 AAT42490 AAT42491 AAX37260 AAX37261 AAX37262 AAX37263 AAX37264 AAV34695 | Add more? | | | treatment of disorders of increased coagulation with or without decreased levels of Protein C. The method is also applicable to other proteins that require post-translational carboxylation.

The present invention will be applicable to improve the productivity of any protein that is dependent on γ-carboxylation, such proteins include, but are not limited to: prothrombin, coagulation factor II (FII), coagulation factor VII (FVII), coagulation factor IX (FIX), coagulation factor X (FX), Protein C, Protein S, Protein Z, Bone Gla protein (also known as: BGP or osteocalcin), Matrix Gla protein (MGP), proline rich Gla polypeptide 1(PRRG1), proline rich Gla polypeptide 2 (PRRG2), Growth arrest-specific protein 6 (Gas 6). Other It will be appreciated that the invention is not restricted to a particular protein or protein encoding sequence of one of these proteins to be co-expressed. Moreover, and in particular with respect to blood coagulation factors, numerous mutant forms of the proteins have been disclosed in the art. The present invention is equally applicable to these mutant forms, including naturally occurring allelic variants, of the proteins as it is to wild-type sequence. In one embodiment the invention can be undertaking with any wild-type protein or one with at least 90%, preferably at least 95% sequence identity thereto.

The sequence identity between two sequences can be determined by pair-wise computer alignment analysis, using programs such as, BestFit, Gap or FrameAlign. The preferred alignment tool is BestFit. In practise, when searching for similar/identical sequences to the query search, from within a sequence database, it is generally necessary to perform an initial identification of similar sequences using suitable software such as Blast, Blast2, NCBI Blast2, WashU Blast2, FastA, Fasta3 and PILEUP, and a scoring matrix such as Blosum 62. Such software packages endeavour to closely approximate the "gold-standard" alignment algorithm of Smith-Waterman. Thus, the preferred software/search engine program for use in assessing similarity, i.e., how two primary polypeptide sequences line up is Smith-Waterman. Identity refers to direct matches, similarity allows for conservative substitutions.

The term vitamin K epoxidoreductase or "VKOR", as used herein, refers to an enzyme that catalyses reduction of vitamin K epoxide and vitamin K to form reduced vitamin K.

Vitamin K reductases are widely distributed, and have been cloned from several different species such as mouse (*Mus musculus*), rat (*Rattus norveigicus*), chicken (*Gallus gallus*) and cow (*Bos taurus*). Homolgous proteins can be predicted from sequences from organsims of widely dispersed phylogenetic origin such as mammals, birds, amphibians, bony fishes, flies, kinetoplastids and bacteria. Table 2 represents a non-limiting list of representative sequences of predicted proteins homologous to human VKOR (sorted after species origin) that can be used in the present invention.

TABLE 2

| Species | Data base accession #/ID |
| --- | --- |
| *Homo sapiens* (man) | NP_775788 |
| | NP_996560 |
| | AAR28759 |
| | AAQ13668 |
| | AAQ88821 |
| | CAH10673 |
| *Bos taurus* (bovine) | NP_001003903 |
| *Mus musculus* (mouse) | NP_848715 |
| | BAB26325 |
| | NP_001001327 |
| *Rattus norveigicus* (rat) | NP_976080 |
| | NP_976083 |
| | AAQ91028 |
| *Gallus gallus* (chicken) | NP_001001328 |
| | NP_996530 |
| *Xenopus laevis* (clawed frog) | AAH43742 |
| | AAH77384 |
| *Xenopus tropicalis* (amphibians) | AAH76993 |
| *Tetraodon nigroviridis* (bony fishes) | CAF98534 |
| | CAG07588 |
| *Takifugu rubripes* (torafugo) | AAR82913 |
| | AAR82912 |
| *Anopheles gambiae* (mosquito) | XP_310541 |
| | EAA06271 |
| *Drosophila melanogaster* (fruit fly) | DAA02561 |
| *Trypanosoma brucei* (protozoa) | XP_340583 |
| *Corynebacterium efficiens* (high GC Gram+ bacteria) | NP_737490 |
| *Corynebacterium glutamicum* (high GC Gram+ bacteria) | NP_600038 |
| *Mycobacterium leprae* (high GC Gram+ bacteria) | NP_302145 |

The term "γ-glutamyl carboxylase" or "GGCX", as used herein, refers to a vitamin K dependent enzyme that catalyses carboxylation of glutamic acid residues.

GGCX enzymes are widely distributed, and have been cloned from many different species such as the beluga whale *Delphinapterus leucas*, the toadfish *Opsanus tau*, chicken (*Gallus gallus*), hagfish (*Myxine glutinosa*), horseshoe crab (*Limulus polyphemus*), and the cone snail *Conus textile* (Begley et al., 2000, ibid; Bandyopadhyay et al. 2002, ibid). The carboxylase from conus snail is similar to bovine carboxylase and has been expressed in COS cells (Czerwiec et al. 2002, ibid). Additional proteins similar to GGCX can be found in insects and prokaryotes such as *Anopheles gambiae, Drosophila melanogaster* and *Leptospira* with NCBI accession numbers: gi 31217234, gi 21298685, gi 24216281, gi 24197548 and (Bandyopadhyay et al., 2002, ibid), respectively. The carboxylase enzyme displays remarkable evolutionary conservation. Several of the non-human enzymes have shown, or may be predicted to have, activity similar to that of the human GGCX we have used, and may therefore be used as an alternative to the human enzyme.

Table 3 identifies representative sequences of predicted proteins homologous to human GGXC (sorted after species origin) that can be used in the present invention.

TABLE 3

| Species | Data base accession #/ID |
| --- | --- |
| *Homo sapiens* (man) | NM_000821.2 |
| | HUMGLUCARB |
| | HUMHGCA |
| | BC004422 |
| | HSU65896 |
| | AF253530.1 |
| *Papio hamadryas* (red baboon) | AC116665.1 |
| *Delphinapterus leucas* (white whale) | AF278713 |
| *Bos taurus* (bovine) | NM_174066.2 |
| | BOVCARBOXG |
| | BOVBGCA |
| *Ovis aries* (domestic sheep) | AF312035 |
| *Rattus norvegicus* (brown rat) | NM_031756.1 |
| | AF065387 |
| *Mus musculus* (mouse) | NM_019802.1 |
| | AP087938 |
| *Opsanus tau* (bony fishes) | AF278714.1 |
| *Conus textile* (molluscs) | AY0044904.1 |
| | AP382823.2 |
| *Conus imperialis* (molluscs) | AF448234.1 |
| *Conus episcopatus* (molluscs) | AF448233.1 |
| *Conus omaria* (molluscs) | AF448235.1 |
| *Drosophila melanogaster* (fruit fly) | NM_079161.2 |
| *Anopheles gambiae* (mosquito) | XM_316389.1 |
| *Secale cereale* (monocots) | SCE314767 |
| *Triticum aestivum* (common wheat) | AF280606.1 |
| *Triticum urartu* (monocots) | AY245579.1 |
| *Hordeum vulgare* (barley) | BLYHORDCA |
| *Leptospira interrogans* (spirochetes) | AE011514.1 |
| *Streptomyces coelicolor* (high GC Gram+ bacteria) | SCO939109 |
| | SCO939124 |
| | AF425987.1 |
| *Streptomyces lividans* (high GC Gram+ bacteria) | SLU22894 |
| *Streptomyces viginiae* (high GC Gram+ bacteria) | SVSNBDE |
| *Micrococcus luteus* (high GC Gram+ bacteria) | MLSPCOPER |
| *Chlamydomonas reinhardtii* (green algae) | AF479588.1 |
| *Dictyostelium discoideum* (slime mold) | AC115612.2 |
| *Coturnix coturnix* (birds) | AF364329.1 |
| *Bradyrhizobium japonicum* (α-protoebacteria) | AP005937.1 |
| *Rhodobacter sphaeroides* (α-proteobacteria) | RSY14197 |
| *Sinorhizobium meliloti* (α-proteobacteria) | RME603647 |
| | AF119834 |
| *Mesorhizobium loti* (α-proteobacteria) | AP003014.2 |
| *Chromobacterium violaceum* (β-proteobacteria) | AE016910.1 |
| | AE016918.1 |
| *Pseudomonas aeruginosa* (γ-proteobacteria) | AE004613.1 |
| | AF165882 |
| *Xanthomonas axonopodis* (γ-proteobacteria) | AE011706.1 |

TABLE 3-continued

| Species | Data base accession #/ID |
|---|---|
| Human herpesvirus 8 | KSU52064 |
| | KSU75698 |
| | AF305694 |
| | AF360120 |
| | AF192756 |

Each of the above-identified GGCX proteins can be used as the carboxylase enzyme in the present invention.

One way to effect the co-expressed proteins is to use different promoters as part of the respective expression control sequences. The art is replete with examples of different cloning vectors, promoters and other expression control sequences that are capable of expressing heterologous proteins to differing degrees or extents. Recombinant expression technology is suitably advanced such that a person skilled in the art of protein expression is able to select promoters and other control sequences to bring about co-expression of the protein requiring carboxylation, vitamin K epoxidoreductase and, optionally, the γ-carboxylase. The selection of which particular promoters and other expression control sequences to use is a matter of individual choice In one embodiment, the control sequences associated with the protein requiring gamma-carboxylation comprise a strong promoter. In one embodiment this is the human cytomegalovirus (hCMV) immediate-early promoter. A strong promoter is here defined as a promoter giving rise to at least 5-fold higher numbers of mRNA transcripts than a weak promoter used in the same cell under similar conditions.

In another embodiment, the control sequences associated with the vitamin K epoxido reductase, and when present the γ-glutamyl carboxylase, comprises a weak promoter. In one embodiment this is SV40 early promoter. In another embodiment the protein requiring gamma-carboxylation and the vitamin K epoxido reductase, and optionally the γ-glutamyl carboxylase, are under the control of different promoter elements with the promoter controlling expression of the vitamin K epoxido reductase, and optionally the γ-glutamyl carboxylase, being weaker that the promoter controlling expression of the protein requiring gamma-carboxylation.

The invention has been exemplified by use of the strong CMV promoter (Boshart et al. Cell 41:521-530, 1985) to over-express Factor X and the weaker SV40 promoter (Wenger et al. Anal Biochem 221:416-418, 1994) to control the expression of vitamin K epoxido reductase and optionally the GGCX expression. Other strong promoter that could be used according to the present invention include, but are not limited to, pEF-1α [human elongation factor-1α subunit gene) (Mizushima and Nagata, Nuc Acids Res 18:5322,1990; Goldman et al., BioTechniques 21:1013-1015, 1996)], pRSV [Rous sarcoma virus (Gorman et al ., Proc Natl Acad Sci USA 79:6777-6781 ,1982)] and pUbC [human ubiquitin (Schorpp et al, Nuc Acids Res 24:1787-1788,1996)].

The invention also extends to purified gamma carboxylated protein produced by the methods of the present invention and their use in coagulant therapy.

According to yet another aspect of the invention there is provided a method of promoting increased or decreased coagulation in a subject comprising administering a pharmacologically effective amount of an isolated gamma-carboxylated protein obtained by the above-described methods to a patient in need thereof.

According to a further aspect of the invention there is provided a method of producing a pharmaceutical composition suitable for inducing blood clotting, comprising purifying active carboxylated protein expressed from a host cell adapted to express a protein requiring gamma-carboxylation and γ-glutamyl carboxylase in a ratio of at least 5:1 and admixing the purified carboxylated protein with one or more pharmaceutically acceptable carriers or excipients.

The compositions of the invention may be obtained by conventional procedures using conventional pharmaceutical excipients, well known in the art, but will most likely be in a form suitable for injection, either parenterally or directly into the wound site.

Powders suitable for preparation of an aqueous preparation for injection, by the addition of a suitable diluent, generally contain the active ingredient together with suitable carriers and excipients, suspending agent and one or more stabilisers or preservatives. The diluent may contain other suitable excipients, such as preservatives, tonicity modifiers and stabilizers.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate.

The pharmaceutical compositions of the invention may also be in the form of a sterile solution or suspension in a non-toxic parenterally acceptable diluent or solvent, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

For further information on Formulation the reader is referred to Chapter 25.2 in Volume 5of Comprehensive Medicinal Chemistry (Corwin Hansch; Chairman of Editorial Board), Pergamon Press 1990; or, Volume 99 of Drugs and the pharmaceutical sciences; Protein formulation and delivery (Eugen J. McNally, executive editor), Marcel Dekker Inc 2000.

The amount of active ingredient that is combined with one or more excipients to produce a single dosage form will necessarily vary depending upon the host treated and the particular route of administration. For example, a formulation intended for injection to humans will generally contain, for example, from 0.2 mg to 6 g or from 0.5 mg to 2 g of active agent compounded with an appropriate and convenient amount of excipients which may vary from about 5 to about 98 percent by weight of the total composition. Dosage unit forms will generally contain about 0.2 mg to about 10 g or about 1 mg to about 500 mg of the active ingredient. Proteinaceous therapeutics are usually stored frozen or freeze-dried. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound will naturally vary according to the nature and severity of the conditions, the age and sex of the animal or patient and the route of administration, according to well known principles of medicine. In using a compound for therapeutic or prophylactic purposes it will generally be administered so that a daily dose in the range, for example, 20 µg to 75 mg per kg body or from 0.5 mg to 75 mg per kg body weight is received, given if required in divided doses. In general lower doses will be administered when a parenteral route is employed. Thus, for example, for intravenous administration, a dose in the range, for example, 20 µg to 30 mg per kg body weight or from 0.5 mg to 30 mg per kg body weight will generally be used. Similarly, for administration by inhalation, a dose in the range, for example, 20 µg to 30mg per kg or from 0.5 mg to 25 mg per kg body weight will be used. As an alternative the compound can be administered as an infusion of 1 µg-10 mg per kilo body weight and hour during a time period of a few hours to several days.

EXPERIMENTAL SECTION

The invention will be further described by the following non-limiting examples.

The practice of the present invention will employ, unless otherwise indicated, conventional methods of molecular biology and recombinant DNA techniques within the skill of the art.

Such techniques are explained fully in the literature. See, e.g., Sambrook et al., eds., Molecular Cloning: A Laboratory Manual (3rd ed.) Cold Spring Harbor Laboratory Press, Cold Spring Harbor, N.Y. (2001); Ausubel et al., eds., Current Protocols in Molecular Biology, John Wiley & Sons, New York, N.Y. (2002); Glover & Hames, eds., DNA Cloning 3: A Practical Approach, Vols. I, II, & III, IRL Press, Oxford (1995); Colowick & Kaplan, eds., Methods in Enzymology, Academic Press; Weir et al., eds., Handbook of Experimental Immunology, 5th ed., Blackwell Scientific Publications, Ltd., Edinburgh, (1997).

Example 1

To investigate the importance of VKOR in expression of carboxylated proteins we have expressed human coagulation factor X (FX) in CHO cells. Fully functional FX has been expressed earlier by Camire et al. 2000 (Biochemistry 39:14322-14329) who obtained approximately 1 µg carboxylated FX per million cells and day, and by Himmelspach et al 2000 (Thromb Res 97:51-67) who claimed obtaining up to 25% (19.5 µg) active FX per million cells and day using a CHO cell line that has been subjected to DHFR amplification. Himmelspach et al. reported incomplete processing of recombinant FX and the maximal productivity of active FX actually shown was 5 µg/ml culture medium In both publications cells were grown as adherent cells in serum-containing medium. Cells were grown to desired confluence, the medium replaced with serum free medium and incubation continued to allow accumulation of product. The amount of product was then estimated from this "serum-free" medium. This culture procedure is not suitable for large scale protein production as the cells will only produce product for a short period. In addition the product will be contaminated with serum proteins such as bovine FX which is highly undesirable as serum proteins will be difficult to remove and may cause antibody formation if present in a product injected to patients The obtained cell lines have thus not been shown suitable for commercial production of pharmaceutical FX.

Establisment of Stable Cell Lines Producing Recombinant Human Factor X

The FX coding sequence was PCR amplified from human liver cDNA using primers:

```
F10F1: 5'-CACACCATGGGGCGCCCACT-3'    (SEQ ID NO: 2)

F10R1: 5'-GAGTGGGATCTCACTTTAATGGA-3' (SEQ ID NO: 3)
```

Cloning of the PCR product was first done by TA-TOPO cloning into pCDNA3.1-V5His (Invitrogen). Clones containing the correct FX sequence were identified by DNA sequencing and by transient expression in COS-7 cells. A blunt-end fragment containing the FX encoding sequence was then cloned into the EcoRV-digested and phosphatase—treated expression vector nopA. Obtained F10nopA (SEQ ID NO:6) clones were verified by DNA sequencing of the inserted sequence and by transient expression in COS-7.

The VKOR coding sequence was PCR amplified from human liver cDNA using primers:

```
VF1:   5'-CACCATGGGCAGCACCTGGGGGA-3'  (SEQ ID NO: 4)

VR1:   5'-GCTCAGTGCCTCTTAGCCTT-3'     (SEQ ID NO: 5)
```

Cloning of the PCR product was first done by TA-TOPO cloning into pCDNA3.1-V5His (Invitrogen). Clones containing the correct VKOR encoding sequence (SEQ ID NO:1) were identified by DNA sequencing. A HindIII-NotI fragment containing the VKOR sequence was then transferred to the expression vector pZeoSV2+ (Invitrogen) digested with the same enzymes. VKORzeo clones (SEQ ID NO:7) obtained were verified by DNA sequencing.

CHO-S cells (Invitrogen) were grown in DMEM F12 medium containing Glutamax I and 9% heat treated FBS, essentially as recommended by Invitrogen. Transfection of CHO-S was done with PvuI-digested (linearized) F10nopA, SspI-digested VKORzeo and Lipofectamine 2000 essentially as recommended by Invitrogen. The DNA transfection mix contained a 1.6-fold molar excess of F10NopA compared to VKORzeo. On the day after transfection, transfected cells were seeded in selection medium; growth medium plus 400 µg/ml G418, to 96-well plates. The VKORzeo construct was thus not selected for, but was randomly integrated in the G418-resistant transfectants. Following days plates were inspected to confirm that a suitable number of clones per well (5-10) were obtained. Six days post transfection the selection medium was replaced by growth medium supplemented with Vitamin K (1 µg/ml). The next day plates were sampled and assayed for FX activity using an assay based on Russels' Viper Venom (RVV-X), which activates FX to FXa. FXa activity was then measured using a chromogenic substrate (S2765, Chromogenix, Mölndal, Sweden). The RVV-X assay is eqivalent to the assay used by Himmelspach et al. for the same purpose. Wells with the highest activity were identified and the clones contained were expanded and subjected to limiting dilution cloning. After limiting dilution cloning and selection of the best clones, chosen clones were expanded and transferred to growth in protein-free medium (CD-CHO supplemented as recommended by Invitrogen plus 1 µg/ml vitamin K). Productivity of recombinant FX was estimated from T-flask cultures. The expression of VKOR was assayed by ReatTime PCR analyses. It was found that all selected clones expressing fully active FX also expressed VKOR. From this we conclude that co-expression of VKOR improves the expression of fully active human coagulation Factor X. The obtained cell lines grow well in protein and animal component free medium and produce FX in the absence of antibiotic selection pressure. Obtained cell lines are therefore considered suitable for large scale protein production and are capable of producing high amounts of active FX. The share of fully active FX is also significantly higher than previously reported.

Example 2

Analyses of Productivity and mRna Ratios for Co-Expression of FX, VKOR and GGCX

Clones obtained in Example 1 were grown in T-flasks in protein free chemically defined CHO medium without antibiotics (Invitrogen). Samples were collected from 4 day cultures for preparation of cDNA and samples for productivity estimates were collected from cultures 5 days after routine split. Control samples were also prepared from the parent non-transfected CHO-S cell line grown in the same medium and analyses of the control samples gave the expected results. Spinner cultures were grown in CD-CHO with or without supplementation of animal component free additives. The amount of active rhFX was estimated by an assay based on RVV-X as in example 1, and a standard of serially diluted purified plasma derived human Factor X (Haematologic Technologies Inc., Vermont, USA). RNA was isolated with Trizol™ according to the protocol supplied by the vendor, Invitrogen. The isolated RNA was DNaseI treated with the kit DNA-free™ from Ambion. cDNA synthesis was carried out using hexamer primers and kit contents from Superscript™ First-Strand Synthesis System for RT-PCR (Invitrogen). Primers and Vic-labeled probes for Real-Time RT-PCR were selected using the software Primer Express™ from Applied Biosystems.

Human γ-Carboxylase Oligonucleotides

| | |
|---|---|
| 5' ACACCTCTGGTTCAGACCTTTCTT 3'<br>Forward primer | (SEQ ID NO: 8) |
| 5' AATCGCTCATGGAAAGGAGTATTT 3'<br>Reverse primer | (SEQ ID NO: 9) |
| 5' CAACAAAGGCTCCAGGAGATTGAACGC 3'<br>Probe | (SEQ ID NO: 10) |

Human Factor X Oligonucleotides

Primers were manufactured by Operon/Qiagen and the probes were ordered from Applied Biosystems.

| | |
|---|---|
| 5' CCGCAACAGCTGCAAGCT-3'<br>Forward primer | (SEQ ID NO: 11) |
| 5' TGTCGTAGCCGGCACAGA-3'<br>Reverse primer | (SEQ ID NO: 12) |
| 5' CAGCAGCTTCATCATCACCCAGAACATG<br>Probe | (SEQ ED NO: 13) |

Human VKOR Oligonucleotides

| | |
|---|---|
| 5' GCTGGGCCTCTGTCCTGAT-3'<br>Forward primer | Seq(SEQ ID NO: 14) |
| 5' ATCCAGGCCAGGTAGACAGAAC-3'<br>Reverse primer | Se(SEQ ID NO: 15) |
| 5' CTGCTGAGCTCCCTGGTGTCTCTCG<br>Probe | S(SEQ ID NO: 16) |

Rodent GAPDH control primers and probe were also used (Applied Biosystems; ABI #4308318 TaqMan® Rodent GAPDH Control Reagents Protocol)—Amplicon length 177 bp. The Real-Time RT-PCR reactions were performed on the 7500 Real Time PCR System, Applied Biosystems. The expected length of the amplified PCR products was confirmed on agarose gels.

TABLE 4

Results from Real-Time PCR analyses of FX expressing clones.

| Clone name | FX mRNA/cell | VKOR mRNA/cell | GGCX mRNA/cell | GAPDH mRNA/cell |
|---|---|---|---|---|
| FX1-5 | 137 | 0.62 | 1 | 1553 |
| FX2-5 | 13 | 0.48 | 0.26 | 2985 |
| FX3-9 | 3 | 0.03 | 0.17 | 1891 |
| FX6 | 267 | 3 | 11 | 2289 |
| FX17-2 | 319 | 2 | 37 | 2381 |

TABLE 5

Productivity estimates and mRNA ratios. Ratios are calculated from data in table 4. Productivity was estimated from activity assays of diluted culture samples.

| Clone name | Ratio FX:VKOR | Ratio FX:GGCX | Active FX μg/ml T-flask | Active FX μg/ml spinner |
|---|---|---|---|---|
| FX1-5 | 221:1 | 137:1 | 0.5 | Not done |
| FX2-5 | 27:1 | 50:1 | 2.4 | Not done |
| FX3-9 | 100:1 | 18:1 | 0.8 | Not done |
| FX6 | 89:1 | 24:1 | 6.9 | 14 |
| FX17-2 | 160:1 | 9:1 | 8.7 | 21 |

The productivities listed in Table 5 are all above those previously obtained from non-amplified cell lines. Esimates of total FX concentration, including inactive FX, was done using a Biacore assay and by SDS-PAGE and Western blotting.

Biacore Assay for the Estimation of the Concentration of Total rhFX

The BIAcore3000™ analytical systems, the running buffer (10 mM HEPES, 0.15 M NaCl, 3.4 mM EDTA and 0.05% P20, pH 7.4), rabbit anti-mouse Fc in 0.15 M NaCl (RAM Fc, lot no. 610) and the CM5 sensor chips were purchased from Biacore AB (Uppsala, Sweden). The procedure was run at 5 μl/min at 25° C. A standardised amine coupling procedure (35 μl activation time) at 25° C. was used to covalently couple 11000 RU of the capturing antibody RAMFc (35 μl, 30 μg/ml in 10 mM sodium-acetate, pH 5.0) to channel 4 of the CMS chip. After immobilisation the surface was regenerated with 5 μl 10 mM glycine buffer pH 1.8 and further equilibrated with the running buffer. With a 20 μl flow of the mouse anti-FX monoclonal IgG antibody N77121M (Biodesign, Maine, USA) (diluted 1/100 in running buffer) 660 RU was captured. Binding of FX in medium resulted in a very stable complex with negligible dissociation. For each new sample of FX the RAM Fc surface was reproducibly regenerated for multiple sandwich experiments. The difference in RU between channel 4 with coupled RAM Fc and channel 3 with a clean surface was used to quantify the binding of 5 μl FX. A standard (2, 4, 6, 8, 10, 15 and 20 μg/ml in medium) of pdFX from Haematologic Technologies Inc. (Vermont, USA) was run and the difference in RU was plotted against the concentration of phFX and the equation for one binding site was fitted to the data. The difference in RU of the unknown samples was used to calculate the concentration of rhFX from the standard curve.

TABLE 6

Share of fully active rhFX produced. Total amount of rhFX was estimated from spinner culture samples using a Biacore assay and amount of active rhFX was estimated by an RVV-X assay. All samples are from spinner cultures in animal component free growth medium.

| Clone/sample | Total FX µg/ml (Biacore assay) | Active FX µg/ml (RVV-X) | % active FX |
|---|---|---|---|
| FX17-2/p050131 | 18.6 | 10.1 | 54 |
| FX17-2/p050202 | 20.6 | 9.6 | 47 |
| FX17-2/p050225 | 11.8 | 12.1 | 103 |
| FX17-2/sp2050309 | 38.3 | 16.3 | 43 |
| FX17-2/sp1050309 | 25.1 | 13.6 | 54 |
| FX17-2/sp2050310 | 39.7 | 21.1 | 53 |
| FX17-2/sp1050310 | 28.1 | 13 | 46 |

Results in table 6 indicates that co-expression of VKOR enhances the expression of fully active rhFX. The high share (43-103%) of fully active rhFX is in agreement with data from SDS-PAGE, Western blot and protein purification.

Example 3

Co-expression of Human Prothrombin, GGCX and VKOR

To obtain a cell line capable of producing high levels of fully active human prothrombin (hFII) we have earlier co-expressed the vitamin K dependent modification enzyme γ-glutamyl carboxylase (GGCX) and hFII. Using this strategy we obtained the P1E2 clone. P1E2 is a highly productive clone expressing rhFII, but, although expression of correctly modified rhFII is vastly improved compared to other FII-producing clones, still only 20-60% (depending on the culture conditions) of the total amount of this rhFII produced is fully γ-carboxylated. In an attempt to further improve the level of fully γ-carboxylated rhFII and hence lower the production costs of rhFII, a new expression strategy was tested using vitamin K epoxide reductase (VKOR). We have cloned VKOR into two different vectors under the control of two different promoters; pCMV in the pHygro vector and pSV40 in the pZeo vector. In CHO-cells, the pCMV promoter is estimated to have an ~6x higher promoter activity than the pSV40 promoter. Both constructs were used in two separate co-transfections to obtain rhFII producing cell lines.

Cell Line Development and Productivity Estimates

Figure 2:
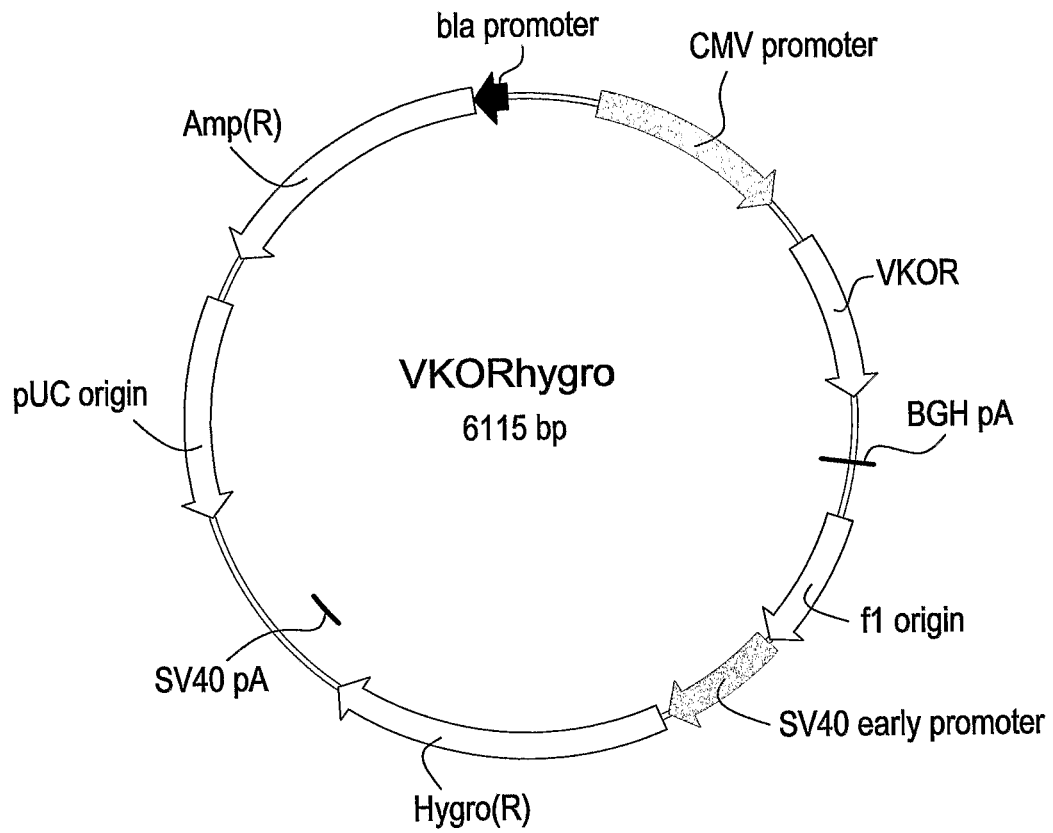
FIG. 2 shows plasmid maps of vectors used for co-expression of FII, GGCX and VKOR
Figure 2:
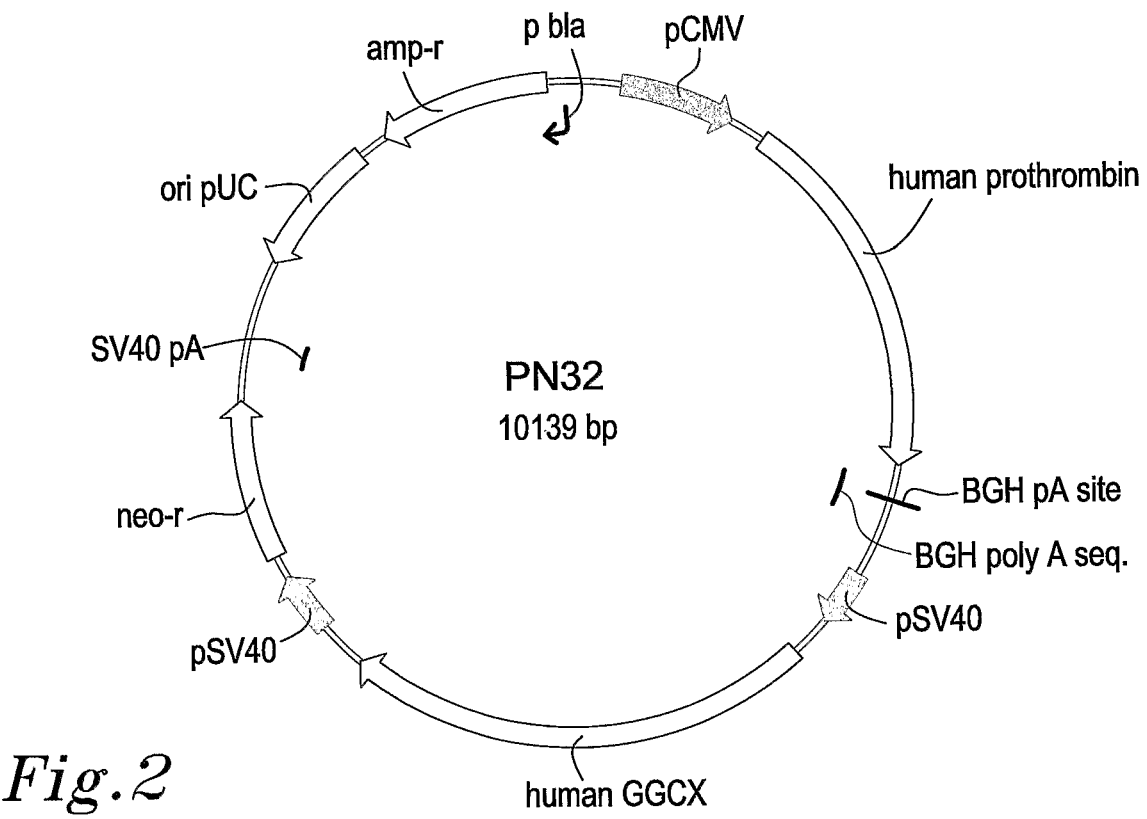
Figure 2:
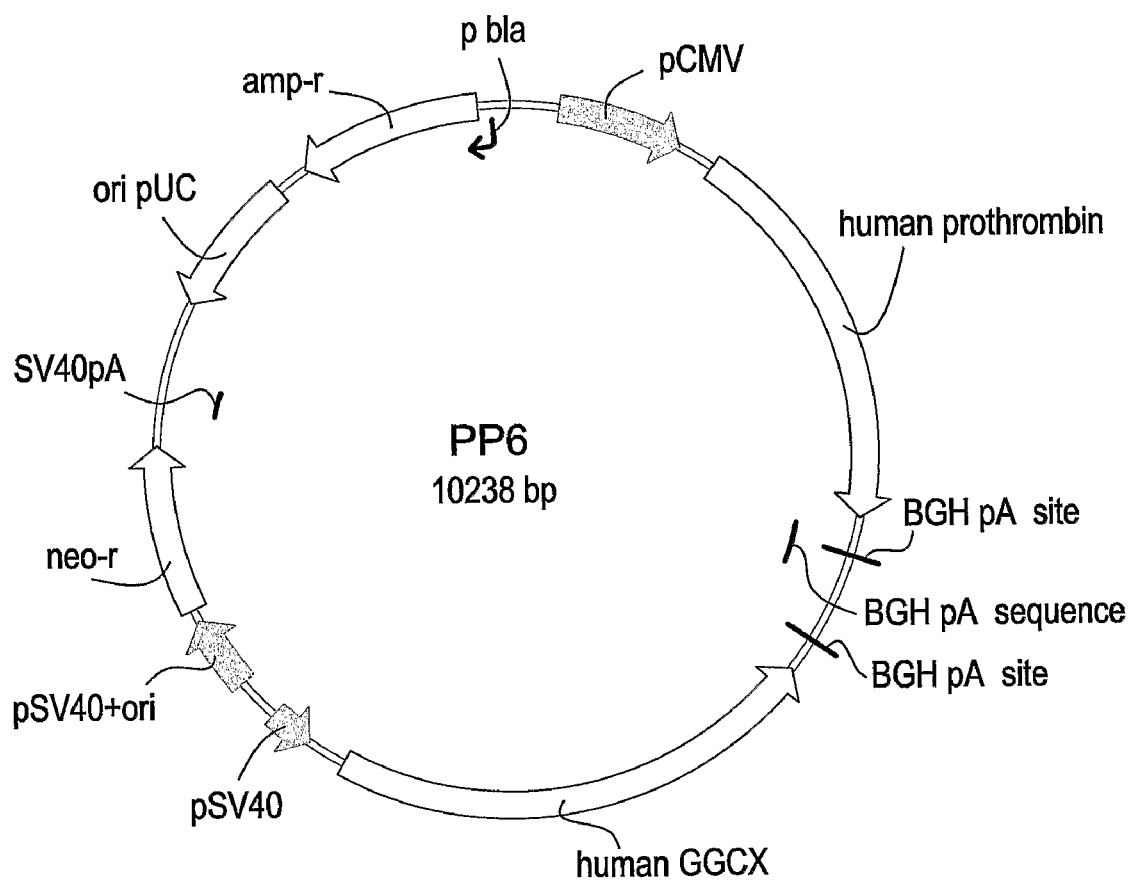

Cell line development was initiated by cotransfecting CHO-S with the PP6 construct (encoding hFII and hGGCX) (SEQ ID NO: 20) and either of the VKOR constructs (FIG. 1-2). Molar ratios used in the transfections were 2:3 (PP6: VKOR). After seeding and selection of transfectants in 96-well plates totally 5500-8500 clones per transfection were then screened using an ecarin based chromogenic-assay. 18 clone pools were selected after the initial screen. After the second screen 9 clone pools were selected, expanded and subjected to a third screening assay. For each transfection the best producing clone pool was selected for limiting dilution. Six 96-well plates were seeded with 0.5 cells/well. 24 clones was selected and upscaled after screening. As the vectors encoding VKOR have not been selected for, Taqman analyses were done to verify VKOR expresssion. In all the three top clones selected; A3F4 (PP6/pZeoVKOR), B11E8 and B9A12 (PP6/pHygroVKOR), VKOR mRNA was detected. Four runs of spinner experiments were done to evaluate and compare the productivity of rhFII for the PP6/VKOR clones compared to the P1E2 clone.

TABLE 7

Production of rhFII in spinner flasks.

| Cell line | Sample ID | Experiment run | Active rhFII (µg/mL) | SPR (pg/cell/day) | Share of active rhFII (active rhFII/total rhFII in %) |
|---|---|---|---|---|---|
| A3F4 | 050317 | A | 10.3 | 1.38 | 100 |
| A3F4 | 050415 | B | 27.6 | 1 | 100 |
| A3F4 | 050425 | C | 23 | 2.6 | 100 |
| B9A12 | 050317 | A | 10.3 | 0.84 | 68 |
| B9A12 | 050413 | B | 27.4 | 1 | 100 |
| B9A12 | 050424 | C | 14.4 | 6.06 | 79 |
| B11E8 | 050317 | A | 13 | 1.74 | 75 |
| B11E8 | 050414 | B | 27.4 | 2.2 | 80 |
| B11E8 | 050424 | C | 22.2 | 4 | 78 |
| P1E2 | 050415 | B | 37.6 | 2.1 | 61 |
| P1E2 | 050424 | C | 25.4 | 2.5 | 21 |

The novel approach to co-express VKOR, GGCX and rhFII resulted in several rhFII-expressing clones producing a much higher share (60-100%) of fully active rhFII compared to the P1E2 clone (20-60%, see table 1). For two of the clones, B11E8 and B9A12 (both PP6/pHygroVKOR cotransfection) a higher specific productivity rate (amount of active protein produced per cell and day, SPR) than the P1E2 clone was obtained under some culture conditions. The A3F4 clone produced 100% fully carboxylated rhFII in all the culture experiments run. This clone has the highest mRNA ratio of both modification enzymes (GGCX and VKOR) to FII compared with the other two clones. However, A3F4 does not produce more fully active rhFII than the other clones.

Example 4

Improved γ-Carboxylation by Supertransfection with VKOR

In a second attempt to use VKOR for improvement of rhFII production, the P1E2 clone (example 3) was modified to co-express VKOR. The pHygroVKOR construct (SEQ ED NO: 22) was in this case used to transfect P1E2 (see Appendix, FIG. 1) and clones were screened for improved productivity by a prothrombinase activity assay. Totally 7000-8000 clones were screened using an end-point prothrombinase assay adapted to 96-well format. Sixteen clone pools were selected after the initial screen. Chosen clone pools were expanded and screened both with both ecarin and prothrombinase assay in order to estimate the share of active rhFII. After this screen 6 clone pools were selected and expanded. The three best producing clone pools were selected for limiting dilution cloning. Twenty-eight clones originating from all three pools were selected and up-scaled after the initial prothrombinase screen. After a second screen, eight clones were selected and up-scaled. Taqman analyses were done to verify VKOR expression in one clone from each cloned pool. In all the three top clones selected (M3F6, P4A4 and O3G3), VKOR mRNA was detected. Three runs of shaker or spinner cultures were done to evaluate the productivity of rhFII for the P1E2/VKOR clones compared to the parent P1E2 clone.

Taqman analyses were done to verify VKOR expression in one clone from each cloned pool. In all three top clones selected; M3F6, P4A4 and O3G3, VKOR mRNA was detected. Because of the selection and screening procedures used to obtain these clones, they are considered to express an optimal level of VKOR expression. This optimal expression level is further characterized in example 5.

TABLE 8

Production of rhFII at peak productivity in spinner/shaker cultures using animal component free media.

| Sample (Clone and Date) | Experiment series | Viable cell densities (cells/ml) | Viability (%) | Total rhFII mg/L | Active rhFII mg/L | Active/total rhFII (%) | SPR; specific productivity rate pg/cell/day |
|---|---|---|---|---|---|---|---|
| P1E2 050622 | A | 1700000 | 87 | 211.9 | 40 | 19 | 7.2 |
| P1E2 050610 | B | 3866666 | 93 | 94.7 | 48.4 | 51 | 1.7 |
| P1E2 051011 | C | 2500000 | nd | 47.9 | 38.4 | 80 | nd |
| M3F6 050622 | A | 2550000 | 83 | 181.6 | 74.7 | 41 | 21.5 |
| M3F6 050609 | B | 1950000 | 59 | 80.2 | 55 | 69 | 1.8 |
| O3G3 050621 | A | 3525000 | >95 | 194.6 | 63.7 | 33 | 3.1 |
| O3G3 050609 | B | 3200000 | 85 | 128.7 | 68.6 | 53 | 4.2 |
| O3G3 051010 | C | 6400000 | nd | 72.8 | 76.8 | 105 | nd |
| P4A4 050621 | A | 2700000 | >95 | 176.9 | 34.1 | 19 | 3.3 |
| P4A4 050610 | B | 2233333 | 81 | 101.6 | 64.2 | 63 | 3.8 |

The P1E2 parent cell line not containing the VKOR construct was grown in paralell under the same conditions as a control.

Results from the culture experiments showed that the amount and share of active rhFII during different culture conditions varied, but for most runs the amount of fully active rhFII produced was better for the novel P1E2/VKOR clones than for the original P1E2 cell line.

Example 5

Establishment of Optimal mRNA Expression Ratios

Messenger RNA prepared from the cell lines in Example 4 and 5 was analysed with Real-Time PCR similarly as in Example 3. For GGCX and VKOR the same oligonucleotides as in Example 3 were used.

Oligonucleotides for prothrombin were:

```
5' TGGAGGACAAAACCGAAAGAGA 3'     (SEQ ID NO: 17)
Forward primer

5' CATCCGAGCCCTCCACAA 3'         (SEQ ID NO: 18)
Reverse primer

5' CTCCTGGAATCCTACATCGACGGGC 3'  (SEQ ID NO: 19)
Probe
```

TABLE 9

Analyses of mRNA ratios at peak expression of human prothrombin (rhFII)

| Cell line | mRNA ratio FII/GGCX | mRNA ratio FII/VKOR | mRNA ratio VKOR/GGCX | Best productivity obtained * (active rhFII mg/L) |
|---|---|---|---|---|
| A3F4 | 5 | 13 | 0.4 | 27.6 |
| B9A12 | 86 | 32 | 3 | 27.4 |
| B11E8 | 29 | 33 | 0.9 | 27.4 |
| M3F6 | 304 | 15 | 20 | 74.7 |

TABLE 9-continued

Analyses of mRNA ratios at peak expression of human prothrombin (rhFII)

| Cell line | mRNA ratio FII/GGCX | mRNA ratio FII/VKOR | mRNA ratio VKOR/GGCX | Best productivity obtained * (active rhFII mg/L) |
|---|---|---|---|---|
| O3G3 | 218 | 17 | 13 | 76.8 |
| P4A4 | 255 | 128 | 2 | 64.2 |
| P1E2 (control without VKOR) | 221 | No VKOR detected | No VKOR detected | 48.4 |

* Measurement of productivity done under similar conditions in spinner or shake flasks.

Results in table 9 indicates that there is an optimal expression level of GGCX and VKOR in relation to the γ-carboxylated protein produced. Clones M3F4, O3G3 and P4A4 were obtained by transfecting P1E2 (earlier obtained by transfection with a construct containing rhFII+GGCX) with a construct containing VKOR under the control of the strong CMV promoter. Screening was perfoimed with an assay specifically detecting clones with an improved productivity of fully active rhFII. Clones with an optimal expression level of VKOR in relation to rhFII and GGCX have thus been selected.

Messenger RNA prepared from the cell lines in Example 4 and 5 was analysed with Real-Time PCR similarily as in Example 3. All analyses included a GAPDH control reaction as in Example 3.

The invention claimed is:

1. An in vitro host cell comprising:
   a first recombinant DNA comprising a sequence encoding a protein requiring gamma-carboxylation operably linked to a first expression control sequence;
   a second recombinant DNA comprising a sequence encoding a vitamin K epoxidoreductase (VKOR) operably linked to a second expression control sequence; and
   a third recombinant DNA comprising a sequence encoding a γ-glutamyl carboxylase operably linked to a third expression control sequence, wherein the protein requiring gamma-carboxylation and the VKOR are expressed, in the cell in a ratio of at least 10:1.

2. The host cell of claim 1, wherein mRNA encoding the protein requiring gamma-carboxylation and mRNA encoding a VKOR are expressed in the cell in a ratio of at least 10:1.

3. The host cell of claim 1, wherein mRNA encoding the protein requiring gamma-carboxylation and mRNA encoding γ-glutamyl carboxylase are expressed in the cell in a ratio of at least 10:1.

4. The host cell of claim 1, wherein the first recombinant DNA encoding a protein requiring gamma-carboxylation and the DNA encoding a γ-glutamyl carboxylase are located on a single expression vector in the cell.

5. The host cell of claim 1, wherein the first recombinant DNA encoding a protein requiring gamma-carboxylation, the second recombinant DNA encoding a VKOR, and the DNA encoding a γ-glutamyl carboxylase are located on a single expression vector in the cell.

6. The host cell of claim 1, wherein the first expression control sequence comprises a first promoter, the second expression control sequence comprises a second promoter, and the activity of the first promoter in the host cell is greater than the activity of the second promoter.

7. The host cell of claim 1, wherein the first promoter is selected from the group consisting of human cytomegalovirus (hCMV) immediate-early promoter, human elongation factor-1 α subunit gene promoter (pEF-1α), Rous sarcoma virus promoter (pRSV), and human ubiquitin promoter (pUbC).

8. The host cell of claim 6, wherein the first promoter is hCMV immediate-early promoter, and the second promoter is SV40 early promoter.

9. The host cell of claim 6, wherein the third expression control sequence comprises a third promoter, and the activity of the first promoter in the host cell is greater than the activity of the third promoter.

10. The host cell of claim 1, wherein the protein requiring gamma-carboxylation is selected from the group consisting of: coagulation factor VII, coagulation factor IX, prothrombin, coagulation factor X, Factor X-like snake venom proteases, Protein C, Protein S, Protein Z, osteocalcin, Matrix Gla protein, and Growth arrest-specific protein 6.

11. The host cell of claim 1, wherein the protein requiring gamma-carboxylation is a vitamin K dependent coagulation factor.

12. The host cell of claim 1, wherein the protein requiring gamma-carboxylation is coagulation factor IX.

13. The host cell of claim 1, wherein the protein requiring gamma-carboxylation is coagulation factor X.

14. The host cell of claim 1, wherein the protein requiring gamma-carboxylation is a Factor X-like snake venom protease.

15. The host cell of claim 1, wherein the protein requiring gamma-carboxylation is prothrombin.

16. The host cell of claim 1, wherein the protein requiring gamma-carboxylation is coagulation factor VII.

17. The host cell of claim 1, wherein the protein requiring gamma-carboxylation is Protein C.

18. The host cell of claim 1, wherein the cell is a mammalian cell.

19. The host cell of claim 1, wherein the cell is a yeast cell or an insect cell.

20. The host cell of claim 1, wherein the cell is a CHO cell, a HEK cell, a NS0 cell, a Per C.6 cell, a BHK cell, or a COS cell.

21. An in vitro cell engineered to express (i) a protein that requires gamma-carboxylation, and (ii) a VKOR, wherein the cell expresses (i) and (ii) in a ratio between 10:1 and 500:1.

22. A method for producing a composition, the method comprising:
   (a) providing a recombinant cell comprising a first nucleic acid sequence encoding a protein requiring gamma-carboxylation operably linked to a first expression control sequence, a second and heterologous nucleic acid sequence encoding a VKOR operably linked to a second expression control sequence, and a third nucleic acid sequence encoding a γ-glutamyl carboxylase operably linked to a third expression control sequence;
   (b) culturing the cell in vitro under conditions suitable for expressing each nucleic acid sequence, wherein (i) the protein requiring gamma-carboxylation and the VKOR are expressed in the cell in a ratio of at least 10:1, and (ii) the protein requiring gamma-carboxylation is carboxylated in the cell, thereby producing a gamma-carboxylated protein; and
   (c) isolating the gamma-carboxylated protein or an activated form thereof.

23. The method of claim 22, further comprising:
   (d) preparing a pharmaceutical composition comprising the isolated gamma-carboxylated protein or an activated form thereof.

24. The method of claim 22, wherein mRNA encoding the protein requiring gamma-carboxylation and mRNA encoding VKOR are expressed in the cell in a ratio of at least 10:1.

25. The method of claim 22, wherein mRNA encoding the protein requiring gamma-carboxylation and mRNA encoding γ-glutamyl carboxylase are expressed in the cell in a ratio of at least 10:1.

26. The method of claim 22, wherein both the first and third nucleic acid sequences are on the same expression vector in the cell.

27. The method of claim 22, wherein the first, second and third nucleic acid sequences are on the same expression vector in the cell.

28. The method of claim 22, wherein the first expression control sequence comprises a first promoter, the second expression control sequence comprises a second promoter, and the activity of the first promoter in the cell is greater than the activity of the second promoter.

29. The method of claim 28, wherein the first promoter is selected from the group consisting of human cytomegalovirus (hCMV) immediate-early promoter, human elongation factor-1α subunit gene promoter (pEF-1α), Rous sarcoma virus promoter (pRSV), and human ubiquitin promoter (pUbC).

30. The method of claim 28, wherein the first promoter is hCMV immediate-early promoter and the second promoter is SV40 early promoter.

31. The method of claim 22, wherein the first expression control sequence comprises a first promoter, the second expression control sequence comprises a second promoter, the third expression control sequence comprises a third promoter, and the activity of the first promoter in the cell is greater than the activity of the third promoter.

32. The method of claim 31, wherein the first promoter is selected from the group consisting of hCMV immediate-early promoter, pEF-1α, pRSV, and pUbC.

33. The method of claim 31, wherein the first promoter is hCMV immediate-early promoter, and the third promoter is SV40 early promoter.

34. The method of claim 31, wherein the activity of the first promoter in the recombinant cell is greater than the activity of each of the second and third promoters.

35. The method of claim 34, wherein the first promoter is selected from the group consisting of hCMV immediate-early promoter, pEF-1α, pRSV, and pUbC.

36. The method of claim 34, wherein the first promoter is hCMV immediate-early promoter, and each of the second and third promoters is SV40 early promoter.

37. The method of claim 22, wherein the cell is a mammalian cell.

38. The method of claim 22, wherein the cell is a yeast cell or an insect cell.

39. The method of claim 22, wherein the cell is a CHO cell, a HEK cell, a NS0 cell, a Per C.6 cell, a BHK cell, or a COS cell.

40. The method of claim 22, wherein the protein requiring gamma-carboxylation is selected from the group consisting of: coagulation factor VII, coagulation factor IX, prothrombin, coagulation factor X, Factor X-like snake venom proteases, Protein C, Protein S, Protein Z, osteocalcin, Matrix Gla protein, and Growth arrest-specific protein 6.

41. The method of claim 22, wherein the protein that requires gamma-carboxylation is a vitamin K dependent coagulation factor.

42. The method of claim 22, wherein the protein that requires gamma-carboxylation is coagulation factor IX.

43. The method of claim 22, wherein the protein that requires gamma-carboxylation is coagulation factor X.

44. The method of claim 22, wherein the protein that requires gamma-carboxylation is a Factor X-like snake venom protease.

45. The method of claim 22, wherein the protein that requires gamma-carboxylation is prothrombin.

46. The method of claim 22, wherein the protein that requires gamma-carboxylation is coagulation factor VII.

47. The method of claim 22, wherein the protein that requires gamma-carboxylation is Protein C.

48. The host cell of claim 1, wherein the protein requiring gamma-carboxylation and the VKOR are expressed in the cell in a ratio between 10:1 and 500:1.

49. The method of claim 22, wherein the protein requiring gamma-carboxylation and the VKOR are expressed in the cell in a ratio between 10:1 and 500:1.

* * * * *

UNITED STATES PATENT AND TRADEMARK OFFICE
CERTIFICATE OF CORRECTION

| | |
|---|---|
| PATENT NO. | : 7,989,193 B2 |
| APPLICATION NO. | : 11/572870 |
| DATED | : August 2, 2011 |
| INVENTOR(S) | : Ann Lövgren |

It is certified that error appears in the above-identified patent and that said Letters Patent is hereby corrected as shown below:

On the Title Page, Column 2 (Other Publications), line 2, delete "[retireved" and insert -- [retrieved --

In Column 61, line 29, in claim 1, delete "expressed," and insert -- expressed --

In Column 61, line 54-55, in claim 7, delete "factor-1 α" and insert -- factor 1α --

Signed and Sealed this
Twenty-seventh Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,989,193 B2 | Page 1 of 1 |
| APPLICATION NO. | : 11/572870 | |
| DATED | : August 2, 2011 | |
| INVENTOR(S) | : Lovgren | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 537 days.

Signed and Sealed this

Twentieth Day of December, 2011

David J. Kappos
*Director of the United States Patent and Trademark Office*